US010942124B2

(12) United States Patent
He et al.

(10) Patent No.: US 10,942,124 B2
(45) Date of Patent: Mar. 9, 2021

(54) SURFACE ENHANCED RAMAN SCATTERING SUBSTRATE ASSEMBLY

(71) Applicant: University of Massachusetts, Boston, MA (US)

(72) Inventors: Lili He, Belchertown, MA (US); Haoxin Chen, Amherst, MA (US); Zhuangsheng Lin, Boston, MA (US)

(73) Assignee: University of Massachusetts, Boston, MA (US)

( * ) Notice: Subject to any disclaimer, the term of this patent is extended or adjusted under 35 U.S.C. 154(b) by 1 day.

(21) Appl. No.: 16/439,186

(22) Filed: Jun. 12, 2019

(65) Prior Publication Data
US 2019/0383747 A1    Dec. 19, 2019

Related U.S. Application Data

(60) Provisional application No. 62/685,102, filed on Jun. 14, 2018.

(51) Int. Cl.
G01N 21/65 (2006.01)
G01N 33/02 (2006.01)

(52) U.S. Cl.
CPC ......... G01N 21/658 (2013.01); G01N 33/025 (2013.01)

(58) Field of Classification Search
CPC .................................................. G01N 21/658
See application file for complete search history.

(56) References Cited

U.S. PATENT DOCUMENTS

| 2006/0038990 A1* | 2/2006 | Habib | G01N 21/658 356/301 |
| 2008/0192247 A1* | 8/2008 | Zerbi | G01N 21/8507 356/301 |
| 2010/0182607 A1* | 7/2010 | Chau | G01N 21/554 356/445 |

FOREIGN PATENT DOCUMENTS

CN    106861600 A  *  6/2017

OTHER PUBLICATIONS

English Machine Translation of CN-106861600-A (Year: 2017).*
Basu, Srismrita, et al., "A needle probe to detect surface enhanced Raman scattering (SERS) within solid specimen", Review of Scientific Instruments 88, 023107 (2017), 5 pgs.
Cialla, Dana, et al., "Surface-enhanced Raman spectroscopy (SERS): progress and trends", Anal Bioanal Chem 403:27-54, (2012), 29 pgs.
Feng, Juanjuan, et al., "Au nanoparticles as a novel coating for solid-phase microextraction", Journal of Chromatography A, 1217 (2010), (2010), 8079-8086.
Glawischnig, Erich, et al., "Camalexin Is Synthesized from Indole-3-Acetaldoxime, a Key Branching Point betweenPrimary and Secondary Metabolism in *Arabidopsis*", Proc. Natl. Acad. Sci., 101, 8245-8250, (2004), 7 pgs.
Harper, Mhairi M., et al., "Recent developments and future directions in SERS for bioanalysis", Phys. Chem. Chem. Phys., 15, 5312-5328, (2013), 17 pgs.

(Continued)

*Primary Examiner* — Dominic J Bologna
(74) *Attorney, Agent, or Firm* — Schwegman Lundberg & Woessner, P.A.

(57) ABSTRACT

The present disclosure provides a surface enhanced Raman scattering substrate assembly for detecting an analyte. The assembly can include an etched fiber base. The assembly can further include a metallic nanoparticle coating disposed over at least a portion of the surface etched fiber base.

19 Claims, 14 Drawing Sheets

(56) References Cited

OTHER PUBLICATIONS

Huang, Jian-An, et al., "SERS-Enabled Lab-on-a-Chip Systems", Adv. Optical Mater., 3, 618-633, (2015), 16 pgs.
Kettles, Graeme J., et al., "Resistance of *Arabidopsis thaliana* to the green peach aphid, *Myzus persicae*, involves camalexin and is regulated by microRNAs", New Phytol., 198, 1178-1190, (2013), 13 pgs.
Kneipp, Janina, et al., "SERS—a single-molecule and nanoscale tool for bioanalytics", Chem. Soc. Rev., 37, 1052-1060. (2008). 9 pgs.
Ko, Hyunhyub, et al., "Nanostructured Surfaces and Assemblies as SERS Media", Small, 4, No. 10, 1576-1599, (2008), 24 pgs.
Larmour, Iain A., et al., "Surface enhanced optical spectroscopies for bioanalysis", Analyst, 136, 3831-3853, (2011), 23 pgs.
Lee, Vincent Yuan-Hsiang, et al., "SERS sample vials based on sol-gel process for trace pesticide analysis", Photonic Detect. Intern. Technol. Safe Food. SPIE 4206:140-147, (2001), 8 pgs.
Mu, Zhongde, et al., "In situ synthesis of gold nanoparticles (AuNPs) in butterfly wings for surface enhanced Raman spectroscopy (SERS)", J. Mater. Chem. B, 1, 1607-1613, (2013), 7 pgs.
Ngo, Ying Hui, "Gold nanoparticles paper as a SERS bio-diagnostic platform", Journal of Colloid and Interface Science 409: 59-65, (2013), 7 pgs.
Qu, Yanqi, et al., "A facile solvent mediated self-assembly silver nanoparticle mirror substrate for quantitatively improved surface enhanced Raman scattering", Analyst. Royal Society of Chemistry 142:4075-4082, (2017), 9 pgs.
Sharma, Dipakshi, et al., "Analytical methods for estimation of organophosphorus pesticide residues in fruits and vegetables: A review.", Talanta. Elsevier B.V. 82:1077-1089., (2010), 13 pgs.
Sharma, H.S. Shekar, "Fabrication of SERS substrate for the detection of rhodamine 6G, glyphosate, melamine and salicylic acid", Vibrational Spectroscopy 83: 159-169, (2016), 11 pgs.
Shende, Chetan S., et al., "Analysis of pesticides on or in fruit by surface-enhanced Raman spectroscopy", Proc. SPIE 5587:170-176, (2004), 8 pgs.
Shende, Chetan, et al., "Inspection of pesticide residues on food by surface-enhanced Raman spectroscopy", Monit. Food Safety Agric. Plant Heal. SPIE 5271:28-35, (2004), 8 pgs.
Vongsvivut, Jitraporn, et al., "Surface-enhanced Raman spectroscopic analysis of fonofos pesticide adsorbed on silver and gold nanoparticles", J. Raman Spectrosc., 41, 1137-1148, (2010), 12 pgs.
Wong, Chi Lok, et al., "Non-labeling multiplex surface enhanced Raman scattering (SERS) detection of volatile organic compounds (VOCs)", Analytica Chimica Acta 844 (2014), 54-60.
Wong, Chi Lok, et al., "Surface-enhanced Raman scattering (SERS)-based volatile organic compounds (VOCs) detection using plasmonic bimetallic nanogap substrate", Appl. Phys. A 117, (2014), 687-692.
Yang, Tianxi, et al., "Investigation of Pesticide Penetration and Persistence on Harvested and Live Basil Leaves Using Surface-Enhanced Raman Scattering Mapping", J. Agric. Food Chem., 65, 3541-3550, (2017), 10 pgs.
Yang, Yaoxia, et al., "Electrodisposition of gold nanoparticles onto an etched stainless steel wire followed by a self-assembled monolayer of octanedithiol as a fiber coating for selective solid-phase microextraction", J. Chromatogr. A 1372:25-33., (2014), 9 pgs.
Zhang, Yida, "Growth of cedar-like Au nanoparticles coating on an etched stainless steel wire and its application for selective solid-phase microextraction", Analytica Chimica Acta 876 (2015), 55-62.
Zheng, Jinkai, et al., "Surface-Enhanced Raman Spectroscopy for the Chemical Analysis of Food", Compr. Rev. Food Sci. Food Saf. 13:317-328, (2014), 13 pgs.
Zhou, Binbin, "Amphiphilic Functionalized Acupuncture Needle as SERS Sensor for In Situ Multiphase Detection", Anal. Chem. 2018,90, (2018), 3826-3832.

\* cited by examiner

SURFACE ENHANCED RAMAN SCATTERING SUBSTRATE ASSEMBLY

CROSS REFERENCE TO RELATED APPLICATION

This application claims the benefit of priority to U.S. Patent Provisional Application No. 62/685,102, filed Jun. 14, 2018, which is incorporated by reference herein in its entirety.

STATEMENT OF GOVERNMENT SUPPORT

This invention was made with Government support under Grant # USDA-NIFA 2016-67017-24458 awarded by the National Institute of Food and Agriculture of the United States Department of Agriculture. The U.S. Government has certain rights in this invention.

BACKGROUND

Surface enhanced Raman scattering (SERS) can be useful for many different applications. For example, SERS can be used to detect a wide variety of biomolecules, metabolites, or other materials. However, a lack of portability of SERS devices and the ability to accomplish real-time detection of analytes are problems with some SERS systems. There is a need therefore, for improving the portability and real-time detection of SERS systems.

SUMMARY OF THE DISCLOSURE

The present disclosure provides a surface enhanced Raman scattering substrate assembly for detecting an analyte. The assembly can include an etched fiber base. The assembly can further include a metallic nanoparticle coating disposed over at least a portion of the surface etched fiber base.

The present disclosure further provides a method for detecting an analyte. The method includes contacting an etched fiber base with a medium. The method further includes contacting the medium with an electromagnetic emission. The method further includes detecting the analyte and generating a spectrum.

The present disclosure further provides a method of making a surface enhanced. Raman scattering substrate assembly for detecting an analyte. The assembly can include an etched fiber base. The assembly can further include a metallic nanoparticle coating disposed over at least a portion of the surface etched fiber base. The method includes etching a fiber to form an etched fiber base. The method further includes coating metallic nanoparticles on the surface of the etched fiber base.

BRIEF DESCRIPTION OF THE FIGURES

The drawings illustrate generally, by way of example, but not by way of limitation, various embodiments discussed in the present document.

DETAILED DESCRIPTION

Figure 1:
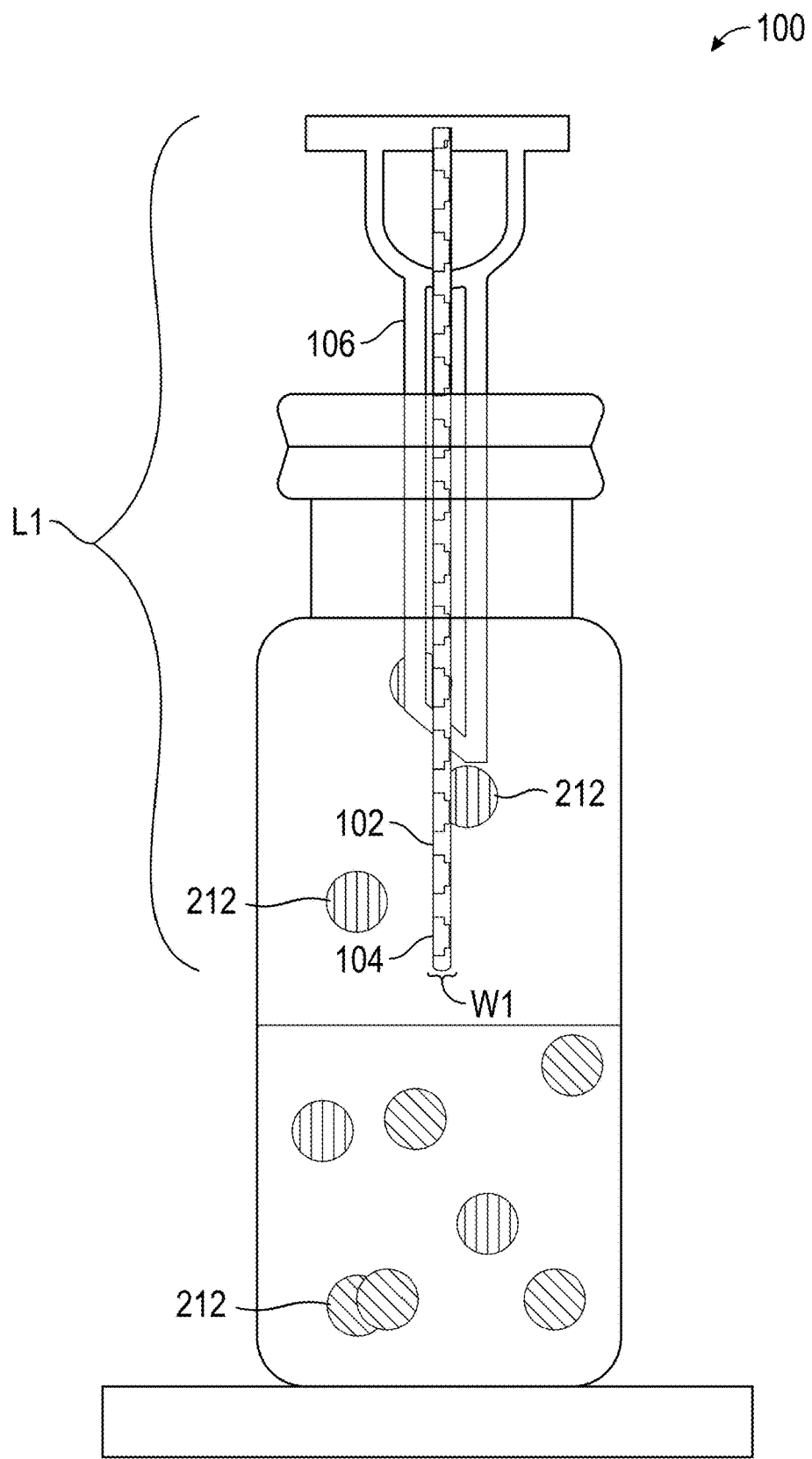
FIG. 1 is a schematic depiction of a surface enhanced Raman scattering substrate assembly, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B". In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Analysis of target compounds (analytes) from complex matrices, such as food or biological samples, is challenging with traditional analytical methods. In particular, interference from other components in the matrices can occur during analysis. For this reason, many analytical processes involved complicated and multi-step sample preparations to improve sensitivity of the analysis. These processes can involve invasive and destructive sampling.

Discussed herein is a method and assembly, in various embodiments, that allows for high speed analysis of analytes in complex matrices without destructive or invasive sampling. The method and assembly can include, in various embodiments, a micro-extraction device enabling in-situ extraction and detection of analytes using surface enhanced Raman spectroscopy (SERS) technology.

FIG. 1 is a schematic depiction of SERS substrate assembly 100. Surface enhanced Raman scattering substrate assembly 100 can include many suitable components for detecting an analyte. Examples of such components for surface enhanced Raman scattering substrate assembly 100 include etched fiber base 102 and metallic nanoparticle coating 104, which is disposed over at least a portion of the surface of etched fiber base 102. Needle 106 at least partially circumscribes etched fiber base 102. Needle 106 is an optional component. If needle 106 is present, needle 106 may be any suitable needle such as a hypodermic needle capable of puncturing a material. Optionally, needle 106 can be used to puncture an opening in the medium, then removed before etched fiber base 102 is inserted. In some embodiments, assembly 100 is in a transparent container to allow SERS analysis.

Etched fiber base 102 can include any suitable material. Factors to consider in choosing the material include the ability etch the material, the durability of the material at elevated temperatures, and the ability of the material to participate in a reduction reaction during coating of the nanoparticles of metallic nanoparticle coating 104. An example of a suitable material for etched fiber base 102 includes stainless steel. In other embodiments, etched fiber base 102 may include copper, lead, chromium, tin, magnesium, aluminum, zinc, manganese, calcium, alloys thereof, and mixtures thereof.

Etched fiber base 102 can have any elongated suitable shape. For example, etched fiber base 102 can be substantially cylindrically shaped, substantially conically shaped, or substantially rectangular shaped. Etched fiber base 102 can have any suitable dimensions with respect to length $L_1$ or width $W_1$. The term "length" is meant to apply to a largest dimension of etched fiber base 102. In some embodiments the etched fiber base has a length ranging from about 3 cm to about 6 cm. The term "width" applies to a largest dimension of etched fiber base 102 substantially orthogonal to the length. In embodiments where etched fiber base 102 is substantially cylindrically shaped, the width may correspond to a largest diameter of etched fiber base 102. In some embodiments the etched fiber base has a width ranging from about 100 µm to about 400 µm or from about 0.5 cm to about 5 cm. Etched fiber base 102 can be, for example, from about 1 cm to about 10 cm (e.g., about 3 cm to about 6 cm). Etched fiber base 102 can have, for example, a thickness of about 50 µm to about 400 µm (e.g., about 50 µm to about 100 µm). Fiber length and thickness can alternatively be determined based on the sample vial or the sample itself, in addition to the needle size if a needle is used.

Etched fiber base 102 can be etched to form a predetermined pattern or a random pattern of grooves, depressions, ridges, pores, or the like. Etching can be accomplished using any suitable method such as acid etching or laser etching. Etching patterns may be formed using a screen or mask to selectively expose certain regions to the etchant.

Etching can be desirable for several reasons. For example, etching a fiber increases the surface area of the fiber as compared to a corresponding fiber that is free of etching, or etched to a lesser degree, that shares substantially the same length and width as etched fiber base 102. The increased surface area can be helpful in embodiments where surface enhanced Raman scattering substrate assembly 100 is used to detect an analyte in a liquid or gaseous phase. This can be because the increased surface area increases the contact points that the analyte has available to interact with upon metallic nanoparticle coating 104. The increased surface area on etched fiber base 102 can further allow for an increased number of metallic nanoparticles to be included in metallic nanoparticle coating 104.

Metallic nanoparticle coating 104 is dispersed over about 50% to about 100% of the total surface area of etched fiber base 102, about 70% to about 100%, about 90% to about 98%, or less than, equal to, or greater than about 70%, 75, 80, 85, 90, 95, or about 100%. Metallic nanoparticle coating 104 includes a plurality of metallic nanoparticles. The total surface area of etched fiber base 102 is the total external surface area inclusive of pores or other non-planar aspects of the surface.

Individual metallic nanoparticles can include any suitable material. For example, individual metallic nanoparticles of the plurality of nanoparticles can include $Ag_2O$, elemental silver, elemental gold, elemental copper, elemental platinum, mixtures thereof, alloys thereof, or combinations thereof. In some embodiments, each metallic nanoparticle is the same material. For example, in some embodiments of surface enhanced Raman scattering substrate assembly 100 each metallic nanoparticle can include elemental gold.

Individual metallic nanoparticles can have any suitable morphology. For example, individual metallic nanoparticles can have a morphology such as a nanosphere, a nanochain, a nanoreef, a nanobox, or a nanostar. In some embodiments, each metallic nanoparticle of metallic nanoparticle coating 104 can have the same morphology. In other embodiments, however, metallic nanoparticle coating 104 can include a mixture of metallic nanoparticles having different morphologies. In some embodiments, surface enhanced Raman scattering substrate assembly 100 can further include a layer of metallic microparticles disposed on etched fiber base 102. Microparticles are generally understood to refer to particles individually having at least one dimeson (e.g., length, width, thickness, diameter, or height) in the micrometer range. The micrometer range can include any distance from about 1 µm to about 1000 µm, about 100 µm to about 500 µm, or less than, equal to, or greater than about 1 µm, 100, 200, 300, 400, 500, 600, 700, 800, 900, or about 1000 µm. Nanoparticles are generally understood to refer to individual particles having at least one dimension (e.g., length, width, thickness, diameter, or height) in the nanometer range. The nanometer range can include any distance from about 1 nm to about 10000 nm, about 100 nm to about 500 nm, or less than, equal to, or greater than about 1 nm, 1000, 2000, 3000, 4000, 5000, 6000, 7000, 8000, 9000, or about 10000 µm. Individual metallic nanoparticles can have any suitable size. For example, a largest dimension of an individual metallic nanoparticle can be in a range of from about 25 nm to about 500 nm, about 50 nm to about 100 nm, or less than, equal to, or greater than about 25 nm, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 400, 405, 410, 415, 420, 425, 430, 435, 440, 445, 450, 455, 460, 465, 470, 475, 480, 485, 490, 495, or about 500 nm.

Etched fiber base 102 having metallic nanoparticle coating 104 disposed thereon can be deployed into an environment as a stand-alone component. Alternatively, etched fiber base 102 having metallic nanoparticle 104 disposed thereon can be at least partially disposed within another component. For example, as shown in FIG. 1, etched fiber base 102 having metallic nanoparticle 104 disposed thereon is at least partially circumscribed and disposed in needle 106. In other embodiments, etched fiber base 102 having metallic nanoparticle 101 disposed thereon can be disposed at least partially within a container such as a straw.

Figure 2A:
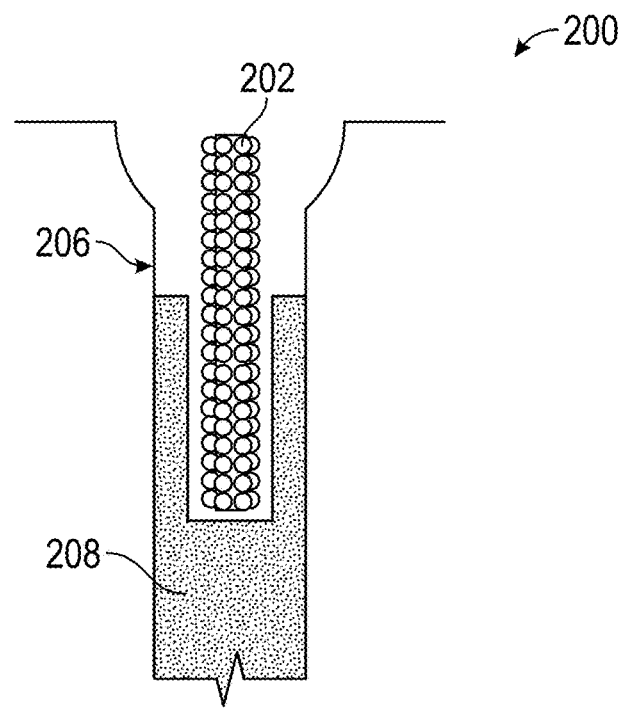
FIGS. 2A-2B are a schematic depictions of a needle for a SERS substrate assembly, in accordance with various embodiments.
Figure 2B:
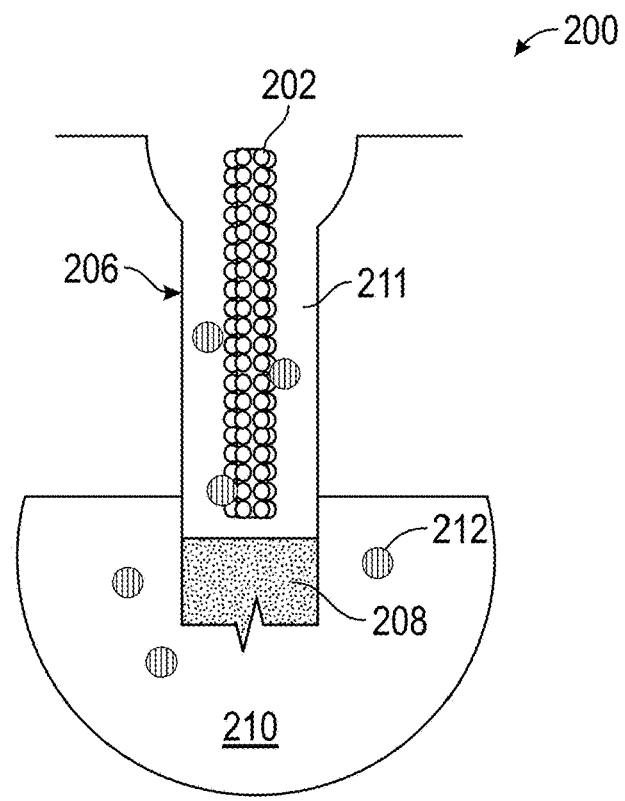

FIGS. 2A-2B are schematic depictions of a needle 206 for a SERS substrate assembly (e.g., assembly 100 in FIG. 1). Needle 206 can include, for example, etched fiber base 202 and metallic nanoparticle coating 204, which is disposed over at least a portion of the surface of etched fiber base 202. Needle 206 at least partially circumscribes etched fiber base 202. Assembly 200 additionally includes in-situ filter 208. Components 202 and 204, are similar to the corresponding components described in reference to FIG. 1 and are connected in a similar fashion.

FIG. 2A shows needle 206 separate from a medium. FIG. 2B shows needle 206 in a medium 210 with analyte 212. The medium in FIG. 2B can be a gaseous medium, a liquid medium, a semi-solid medium, or a medium that is a mixture of states. For example, the medium could be a gaseous or liquid solvent holding an analyte, such as a beverage, or could be the interior of a fruit, vegetable, meat, a dairy product, a grain, or other solid material being tested for analytes as discussed in depth below.

In-situ filter 208 caps needle 206, allowing the medium and analyte to pass through in-situ filter 208 prior to reaching etched fiber base 202 with metallic nanoparticle coating 204. In-situ filter 208 allows analyte to pass to etched fiber base 202 for analysis but prevents impurities (i.e., other components of the medium or matrix) from affecting etched fiber base 202. Examples of impurities include a pesticide, a metabolite, a pathogen, a bacteria, a fungi, a virus, an enzyme, a reactive oxygen species, and a mixture thereof. These are discussed in more detail below. Filtration by filter 208 can be mechanical (e.g., filtration by size of particles or impurities due to pore size of filter 208) or chemical (e.g., filter 208 could include ligands or other chemical components that are likely to capture certain impurities). By reducing impurities, in-situ filter 208 also increases sensitivity of etched fiber base 202 to the analyte of interest.

Needle 206 can be a metallic (e.g., stainless steel copper, lead, chromium, tin, magnesium, aluminum, zinc, manganese, calcium, alloys thereof, and mixtures thereof), or plastic need suitable for puncturing a material for example, a hypodermic needle. Needle 206 can be a hollow needle (e.g., an extraction needle shell). Needle 206 can have, for example, a tapered end to allow for puncturing of a medium. In contrast, etched fiber base 202 can be blunt. In-situ filter 208 can be integral with needle 206, and etched fiber base 202 can be inserted into needle 206. In some embodiments, etched fiber base 202 is aligned with the outside end of needle 206. Alternatively, etched fiber base 202 can extend beyond the outside end of needle 206 (see, for example, FIG. 10).

In-situ filter 208 can, for example, cover just an end of the needle 206, or partially cover the sides of the needle 206, or can fill the end or a portion of needle 206, depending on the extent of protection of etched fiber base 202 desired. In some embodiments, protection of etched fiber base 202 with in-situ filter 208 allows for "naked" etched fiber base 202 without metallic nanoparticle coating 204.

In-situ filter 208 can be a polymeric porous membrane attached to in needle 206. In-situ filter 208 can be made, for example, by a polymer coating that can be cured to the end of needle 206. For example, in-situ filter 208 can be made of cellulose, nitrocellulose, polytetrafluoroethylene (PTFE), nylon, polycarbonate acrylic based polymers, methacrylic based polymers, and combinations thereof. In-situ filter 208 can chemically or physically immobilize active absorbents or catalytic compounds in the medium. Alternatively, the in-situ filter 208 can remove or breakdown interfering compounds from the medium.

Figure 12:
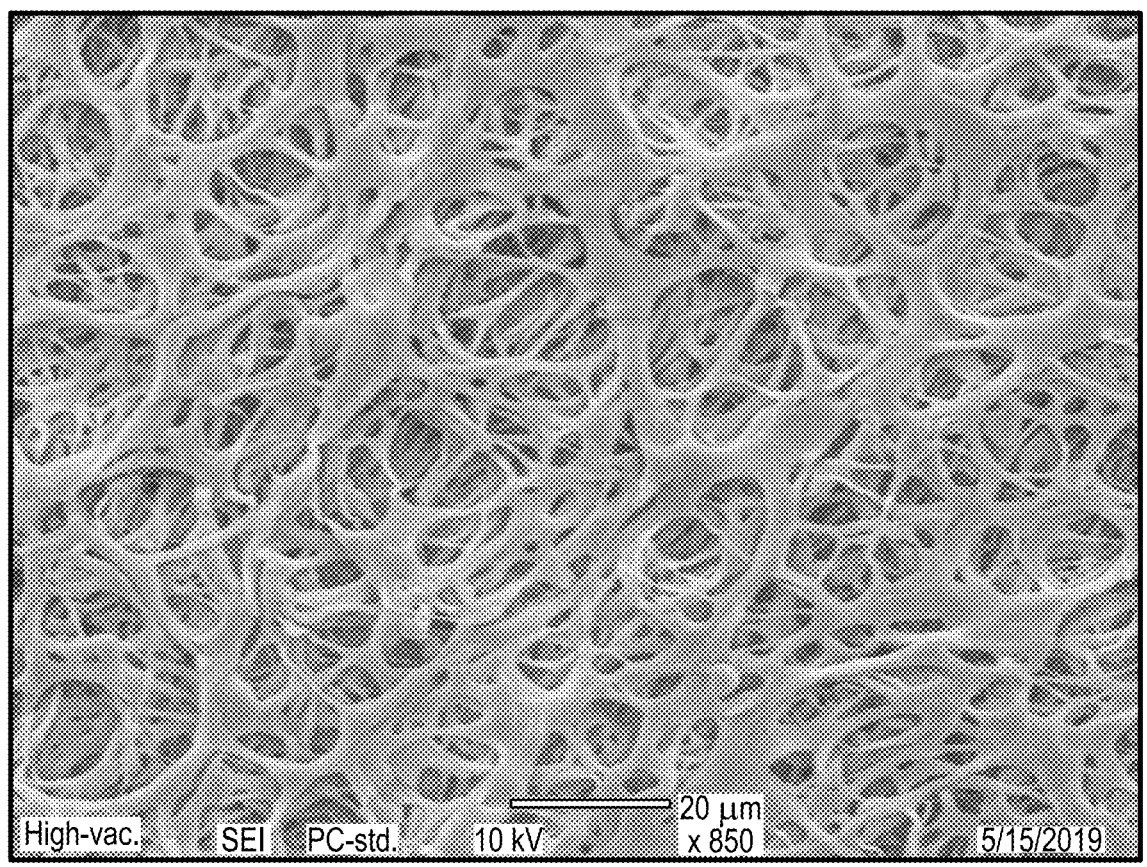
FIG. 12 is an SEM image showing pore size of an in-situ filter, in accordance with various embodiments.

In-situ filter 208 can be a porous material so as to allow passage of the analyte through toward etched fiber base 202. This can also allow in-situ filter 208 to have a large surface area for absorbing or interacting with impurities. FIG. 12 shows an SEM photograph of an example in-situ filter. In-situ filter 208 can have, for example, an average pore size (across the longest point of the pore) of about 5 µm to about 35 µm (i.e., about 10 µm to about 25 µm, preferably from about 12 µm to about 20 µm). In-situ filter 208 allows for passage of medium 212 through into needle 206, where the medium is now filtered medium 211, containing less impurities.

In-situ filter 208 can be pre-prepared and inserted into needle 206 or prepared directly in needle 206 via in-situ polymerization. The in-situ filter 208 can contain a cavity that allows insertion of the etched fiber base 202.

Figure 3:
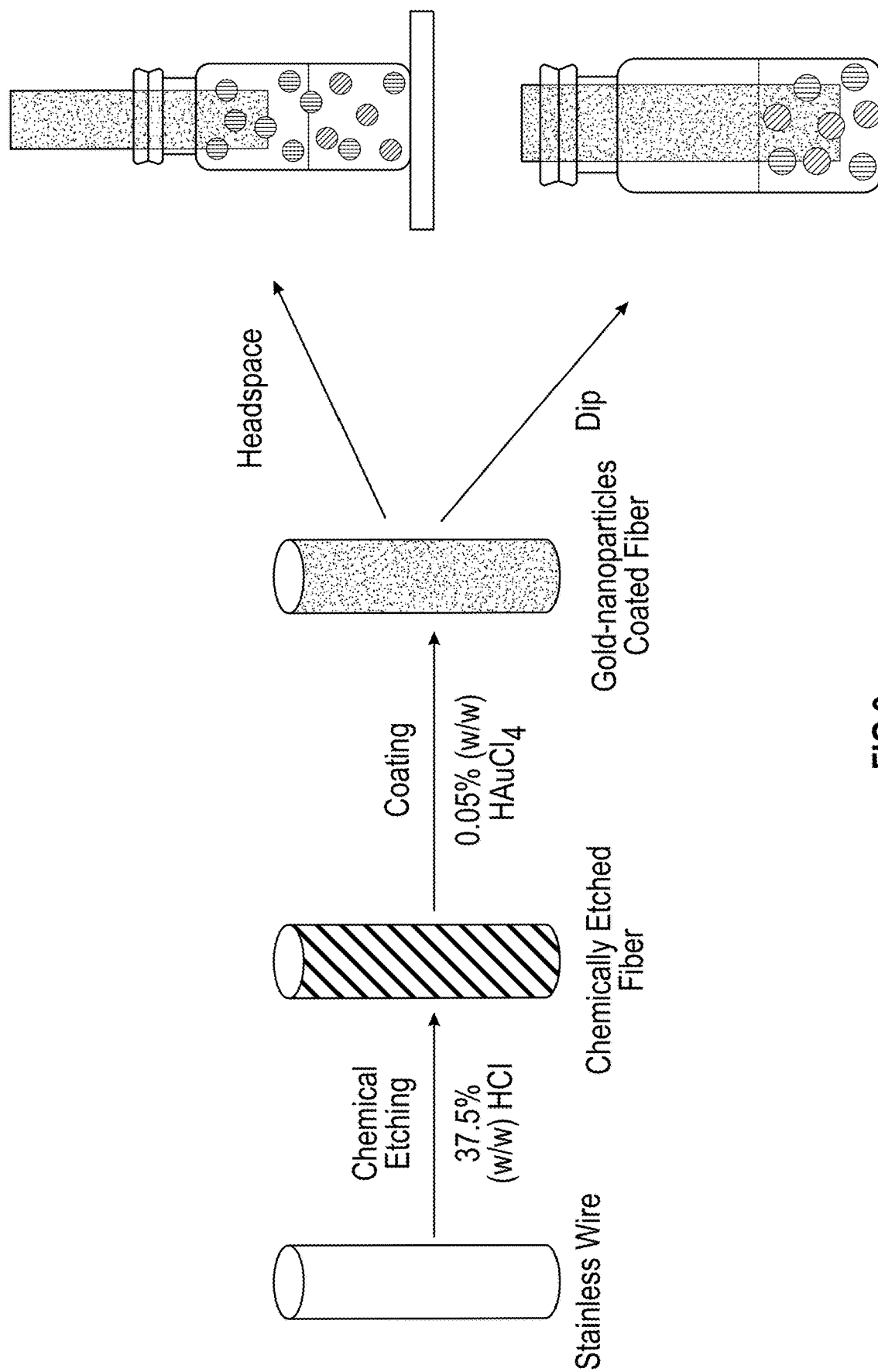
FIG. 3 is a schematic depiction of a method of making and using a surface enhanced Raman scattering substrate assembly, in accordance with various embodiments.

In operation, surface enhanced Raman scattering substrate assembly 100 or 200 can be used to detect an analyte. A method for using surface enhanced Raman scattering substrate assembly 100 or 200, illustrated in FIG. 3, can include contacting etched fiber base 102 or 202 having metallic nanoparticle 104 or 204 disposed thereon with a medium. Etched fiber base 102 or 202 having metallic nanoparticle 104 or 204 disposed thereon can then be removed from contact with the medium and contacted with a laser emission. A spectrum can then be generated and analyzed for the presence or absence of an analyte. The amount of analyte present or the concentration of the analyte in solution can also be quantitatively determined from the spectrum that is generated.

Surface enhanced Raman scattering substrate assembly 100 or 200 can be adapted to collect and subsequently detect an analyte that is in any one of the gaseous phase, liquid phase, or solid phase. To that end, etched fiber base 102 or 202 having metallic nanoparticle 104 or 204 disposed thereon can be disposed in a gaseous phase, a liquid phase, or a solid phase. In some embodiments, substrate assembly 100 or 200 can be disposed in all three phases or any two of the three phases simultaneously. For example, a first region of etched fiber base 102 or 202 can be located in a gaseous phase, a second region of etched fiber base 102 or 202 can be located in a liquid phase (e.g., in an organic liquid phase, in an aqueous liquid phase, or both), and a third region of etched fiber base 102 or 202 can be located in a solid phase. According to some embodiments, each region of etched fiber base 102 or 202 can be specifically configured for collection of analytes in a specific phase. Disposing etched fiber base 102 or 202 across multiple phases can allow for simultaneous collection of analytes on etched fiber base 102 or 202 across those phases.

After the analyte or analytes are collected on etched fiber base 102 or 202, etched fiber base 102 or 202 can be removed for detection of the analyte or analytes by SERS. Alternatively, SERS can be carried out in situ if, for example, substrate assembly 100 or 200 is configured to allow electromagnetic radiation to interact with etched fiber base 102 or 202.

As an example, as shown in FIG. 1, etched fiber base 102 or 202 having metallic nanoparticle 104 or 204 disposed thereon is placed in a sealed environment and is disposed within a gaseous medium. Analytes of interest are collected on etched fiber base 102 or 202. Etched fiber base 102 or 202 can then be analyzed via SERS either by removing etched fiber base 102 or 202 from needle 106 or 206, or as mentioned above, in some cases can be analyzed through assembly 100 or 200 if the vial is transparent to electromagnetic radiation.

Surface enhanced Raman scattering substrate assembly 100 or 200 can be used in conjunction with many different types of analytes. Suitable examples of mediums include a food, a beverage, a plant, an animal, or a mixture thereof. Suitable examples of food include a vegetable, a fruit, a meat, a dairy product, a grain, and mixtures thereof. Suitable examples of beverages include milk, beer, wine, water, juice, coffee, tea, and mixtures thereof. In still further embodiments, the medium can be generated from a living organism. For example, the medium can be living organism's breath. In some embodiments, the medium, and therefore the analyte, can be heated to put the analyte into a gaseous phase for detection.

The analyte can be any analyte of interest. For example, the analyte can be a pesticide, a metabolite, a pathogen, a bacteria, a fungi, a virus, an enzyme, a reactive oxygen species, and a mixture thereof. Examples of a suitable pesticide is O-Ethyl S-phenyl ethylphosphonodithioate (fonofos), thiabendazole, acetamiprid, (iron tris(dimethyldithiocarbamate) (ferbam), phosmet, phorate, isocarbophos, and mixtures thereof. Examples of suitable metabolites include salicylic acid, phytoalexin, sulfonic acid, diphenyl sulfide, allyl methyl sulfide, and a mixture thereof. In general, any compound including sulfur may be an analyte of interest. Examples of a suitable enzyme include an enzyme including adenine (e.g., flavin adenine dinucleotide), nicotinatnide adenine dinucleotide phosphate oxidase. Suitable bacteria for examination may include a gram-positive bacteria, a gram-negative bacteria, and mixtures thereof. In some embodiments, the bacteria is chosen from *Clostridium botulinum, Listeria monocytogenes, Acetic acid bacteria, Acidaminococcus, Acinetobacter Agrobacterium tumefaciens, Akkermansia muciniphila, Anaeroblospirillum, Anaerolinea thermolimosa, Anaerolinea thermophila, Arcobacter, Arcobacter skirrowii, Armatimonas rosea, Azotobacter salinestris, Bacteroides, Bacteroides fragilis, Bacteroides ureolyticus, Bacteroidetes, Bartonella japonica, Bartonella koehlerae, Bartonella Bdellovibrio, Brachyspira, Bradyrhizobium japonicum, Caldilinea aerophile, Cardiobacterium hominis, Chaperone-Usher fimbriae, Christensenella, Chthonomonas calidirosea, Coxiella bumetiid, Cyanobacteria, Cytophaga, Dehalogenimonas lykanthroporepellem, Desulfurobacterium atlanticum, Devosia pacifica, Devosia psychrophila, Devosia soli, Devosia subaequoris, Devosia submarina, Devosia yakushtmensis, Dialister, Dictyoglomus thermophilum, Enterobacter, Enterobacter cloacae, Enterobacter cowanii, Enterobacteriaceae, Enterobacteriales, Escherichia, Escherichia coli, Escherichia fergusonii, Escherichia hermannii, Eimbriimonas ginsengisoli, Elavobacterium, Flavobaclerium akiainvivens, Erancisella novicida, Fusobacterium necrophorum, Fusobacterium nucleatum, Fusobacterium polymorphum, Haemophilus felis, Haemophilus haemolyticus, Haemophilus influenzae, Haemophilus pittmaniae, Helicobacter, Kingella kingae, Klebsiella pneumoniae, Kluyvera ascorbate, Kluyvera cryocrescens, Legionella, Legionella clemsonensis, Legionella pneumophila, Leptonema illini, Leptotrichia buccalis, Levilinea saccharolytica, Luteimonas aquatic, Luteimonas composti, Luteimonas lutimaris, Luteimonas marina, Luteimonas mephitis, Luteimonas vadose, Megamonas, Megasphaera, Meiothermus, Meiothermus timidus, Methylobacterium fujisawaense, Morax-Axenfeld diplobacilli, Moraxella, Moraxella bovis, Moraxella osloensis, Morganella morganii, Mycoplasma spumans, Neisseria cinereal, Neisseria gonorrhoeae, Neisseria meningitidis, Neisseria polysaccharea, Neisseria sicca, Nitrosomonas eutropha, Nitrosomonas halophila, Nonpathogenic organisms, OMPdb, Pectinatus, Pedobacter heparinus, Pelosinus, Propionispora, Proteobacteria, Proteus mirabilis, Proteus penneri, Pseudomonas, Pseudomonas aeruginosa, Pseudomonas luteola, Pseudoxanthomonas broegbernensis, Pseudoxanthomonas japonensis, Rickettsia rickettsia, Salinibacter ruber, Salmonella, Salmonella bongori, Salmonella enterica, Samsonia, Selenomonadales, Serratia marcescens, Shigella, Shimwellia, Solobacterium moorei, Sorangium cellulosum, Sphaerotilus natans, Sphingomonas gei, Spirochaeta, Spirochaetaceae, Sporomusa, Stenotrophomonas, Stenotrophomonas nitrilireducens, Thermotoga neapohtana, Thorselliaceae, Trimeric autotransporter adhesion, Vampirococcus, Verminephrobacter, Vibrio adaptatus, Vibrio azasii, Vibrio campbellii, Vibrio cholerae, Victivallis vadensis, Vitreoscilla, Wolbachia, Yersiniaceae, Zymophilus,* strains thereof, and mixtures thereof.

Detection of any analyte can be used to assess many parameters of a medium. For example, the presence of pesticides can be used to determine whether food is safe for consumption. Detection of certain analytes can be used to generate a profile of a medium. For example, a medium such as wine can be analyzed for certain analytes that can be used to grade wine using artificial analysis. This can be used to perform a uniform analysis of the wine having the subjectivity of a human wine tester removed. As a further example the medium can be a person's breath. The breath can be analyzed for certain analytes that may be indicators of bad breath or certain health issues. Furthermore, the presence of certain analytes such as metabolites can be indicators of biotic stress in a plant. This can be monitored continuously to assess the health of a plant.

Surface enhanced Raman scattering substrate assembly 100 or 200 can be manufactured in many suitable manners. For example, a fiber can be etched to form etched fiber base 102 or 202. As described herein, the fiber can be etched with a laser or by exposing the fiber to an etchant. The etchant can be an acid such as hydrochloric acid.

Following etching, the metallic nanoparticles are coated on the surface of etched fiber base 102 or 202. Coating can be accomplished by at lest partially immersing etched fiber base 102 in a solution comprising the metal of the metallic nanoparticle. The metal in the solution is then reduced thereon. In some embodiments in which metallic nanoparticle layer 104 or 204 includes gold nanoparticles, the solution comprising the metal can be $HAuCl_4$.

In general, the assemblies 100, 200, disclosed herein allow for analysis of target compounds (analytes) in complex mediums such as food or biological samples without complex sampling methods. An in-situ micro-extraction device used with a SERS needle can improve sensitivity to analytes with minimally invasive techniques.

EXAMPLES

Various embodiments of the present disclosure can be better understood by reference to the following Examples which are offered by way of illustration. The present disclosure is not limited to the Examples given herein.

Example 1

In this Example, a highly sensitive surface enhanced Raman scattering method coupled with headspace and solid phase micro-extraction (SPME) to detect volatile pesticide fonofos using an etched fiber having a metallic nanoparticle coating disposed thereon is described. Fonofos, or O-ethyl S-phenyl ethylphosphonodithiolate, is selected as a model for detection using this method because of its volatility (i.e., boiling point is 130° C. at 0.1 mm Hg). It is one of the organophosphate soil insecticides that can control pests such as corn rootworms. According to Environmental Protection Agency regulatory document, the oral exposure to fonofos can induce acethylcholinesterase inhibition and cause acute toxicity. The chronic reference dose for fonofos is 0.002 mg/kg/day, the health reference level is 10 ppb, and the minimum reporting level is 0.5 ppb. A gold-nanoparticle coated fiber was fabricated using a chemical etching and coating method. The characterization of the fabricated fibers and their performance in headspace-SPME and dip-SPME methods followed by SERS analysis were determined in water and complex matrix (i.e. apple juice).

Materials. Analytical grade standard of fonofos (>99.9%), hydrogen tetrachloroaurate hydrate (99.999%), and sodium chloride (>99.5%) were procured from Sigma Aldrich (St. Louis, Mo., USA). Hydrochloric acid (34%-37.5%), Acetonitrile (99.9%), ethanol (100%) and methanol (99.9%) were purchased from Fisher Scientific (Fair Lawn, N.J., USA). The Langres® apple juice was purchased from local Stop & Shop supermarket (Amherst, Mass., USA). The stainless-steel wire (SUS304, φ140 μm) was purchased from the Small Parts, Inc. Stock solution of fonofos was prepared in acetonitrile at 100 ppm and further diluted by distilled water or apple juice.

Preparation of gold nanoparticles-coated fibers. An acid etching reaction was used to increase the roughness of a wire fiber as well as strengthen the binding between the gold-nanoparticles coating and the porous stainless wire with the increased surface. The stainless-steel wire (5 cm) was washed with methanol, ethanol and distilled water in an ultrasonic bath for 10 min respectively and then chemically etched in hydrochloric acid (37.5%) to create the roughness of the wire fiber. The etched fiber was washed again with methanol and distilled water in the ultrasonic bath for 5 min respectively, then dried at 60° C. The etched fiber was then immersed into $HAuCl_4$ solution (0.05%, w/w) to introduce gold to its porous surface as demonstrated in FIG. 3. The coating reaction is the replacement reaction between iron and gold that is shown below.

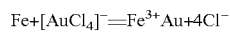

$$Fe+[AuCl_4]^-=Fe^{3+}+Au+4Cl^-$$

The surface morphology of acid-etched fiber and gold-nanoparticles coated fiber were characterized under microscopes and SEM.

Detection of pesticides using headspace-SPME and dip-SPME methods. Each test pesticide stock solution of 100 mg/L (ppm) was prepared with acetonitrile and further diluted to needed concentrations (0.5 ppm to 0.005 ppm) with distilled water or apple juice prior to use. 5 mL of working solution was mixed with 3 mL of 20% sodium chloride solution in a 16-mL vial with an open top polypropylene closure and PTFE/silicone septa. The addition of 20% NaCl solution can increase the ionic strengths and thus decreases the solubility of organic analytes in the aqueous phase in headspace-SPME detection. In the headspace-SPME method, the fiber was inserted through the silicon septum into the headspace above the working solution to extract the volatile compounds. The extraction condition was 75° C. for 30 min. After extraction, the fiber was fixed on a slide for SERS analysis. In the dip-SPME detection, working solution remains the same while the fiber dipped into the working solution without salt for 30 min under room temperature. The fiber was then air-dried and measured using Raman microscopy.

Instruments and data analysis. The surface morphology of etched fiber and gold-nanoparticles coated fiber were characterized by FEI Magellan 400 scanning electron microscope (SEM, Hillsboro, Oreg.) with the voltage of 5.0 kV.

A DXR Raman microscope (Thermo Fisher Scientific, Madison, Wis., U.S.A.) with a 780 nm laser and a 50× confocal microscope objective (0.8 mm spot diameter and 2 $cm^{-1}$ spectral resolution) was used in this study. Each spectrum was scanned from 2000 to 800 $cm^{-1}$ with 1 mW laser power and a 50 mm slit width for 2 seconds integration time. OMNIC™ software version 9.1 was used to control the Raman instrument. Fifteen scans were selected from each fiber and then averaged by the software.

The Raman spectra were analyzed using Thermo Scientific TQ Analyst 8.0 software. All Raman intensities were calculated from at least three replicates and standard deviations were recorded. The peak at 1571 $cm^{-1}$ Raman shift of fonofos was chosen for further characteristic analysis due to its good consistency and least interference with the AuNPs background and apple juice signals.

Figure 4D:
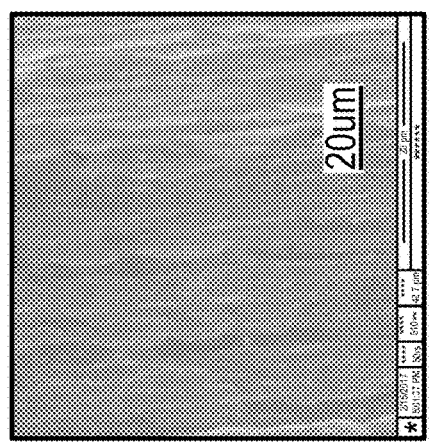
FIGS. 4A-4H are scanning electron microscope (SEM) images showing etched fibers and coated etched fibers, in accordance with various embodiments.
Figure 4C:
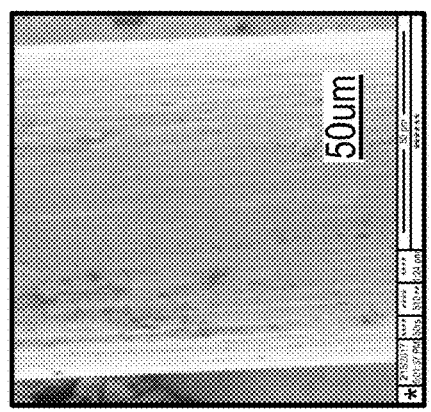
Figure 4B:
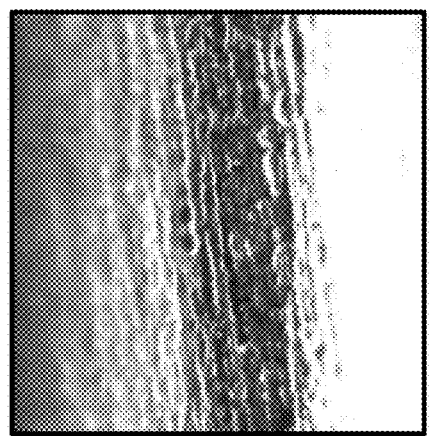
Figure 4A:
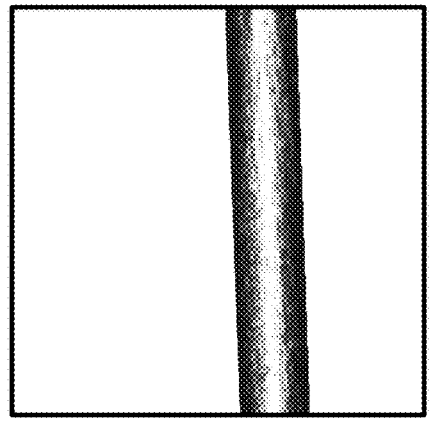
Figure 4H:
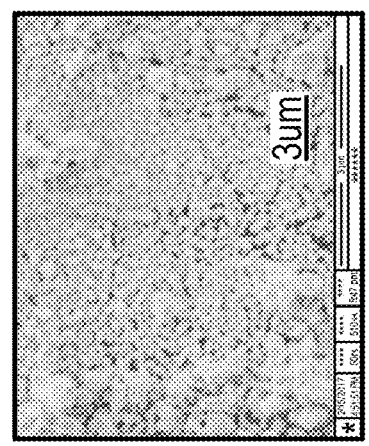
Figure 4G:
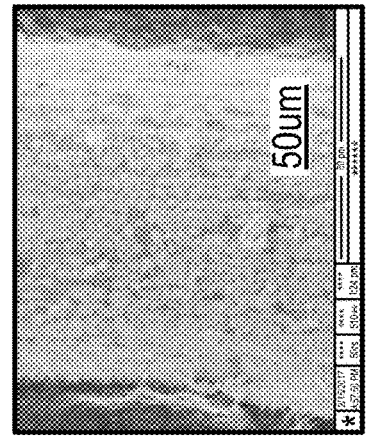
Figure 4F:
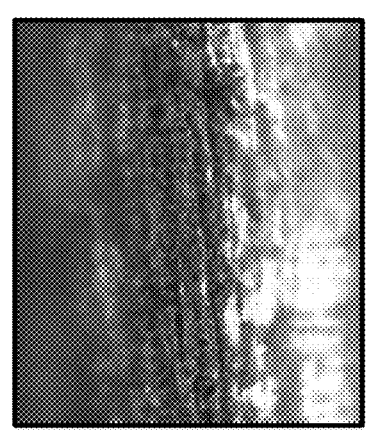
Figure 4E:
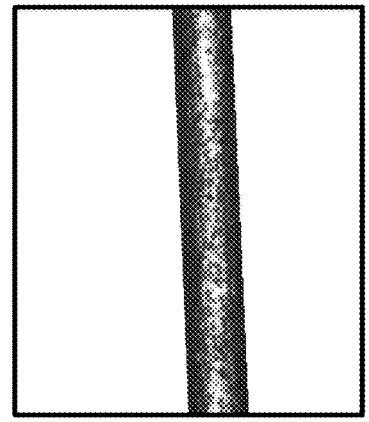

Characterization of fiber substrate and fonofos SERS spectra. The etched fiber has rough surface as shown in FIG. 4A to 4D. After replacement reaction, the coated fiber showed golden color which indicates the successful coating of Au in FIG. 4E and FIG. 4F. Under SEM, the nanoparticles were at around 100 nm and evenly and densely distributed in FIG. 4G and FIG. 4H. This fabrication method shows great advantage as a simple and rapid way for coating nanoparticles onto a stainless-steel fiber comparing to other fabrication methods including laser ablation, annealing and chemical reaction layer by layer.

Figure 5:
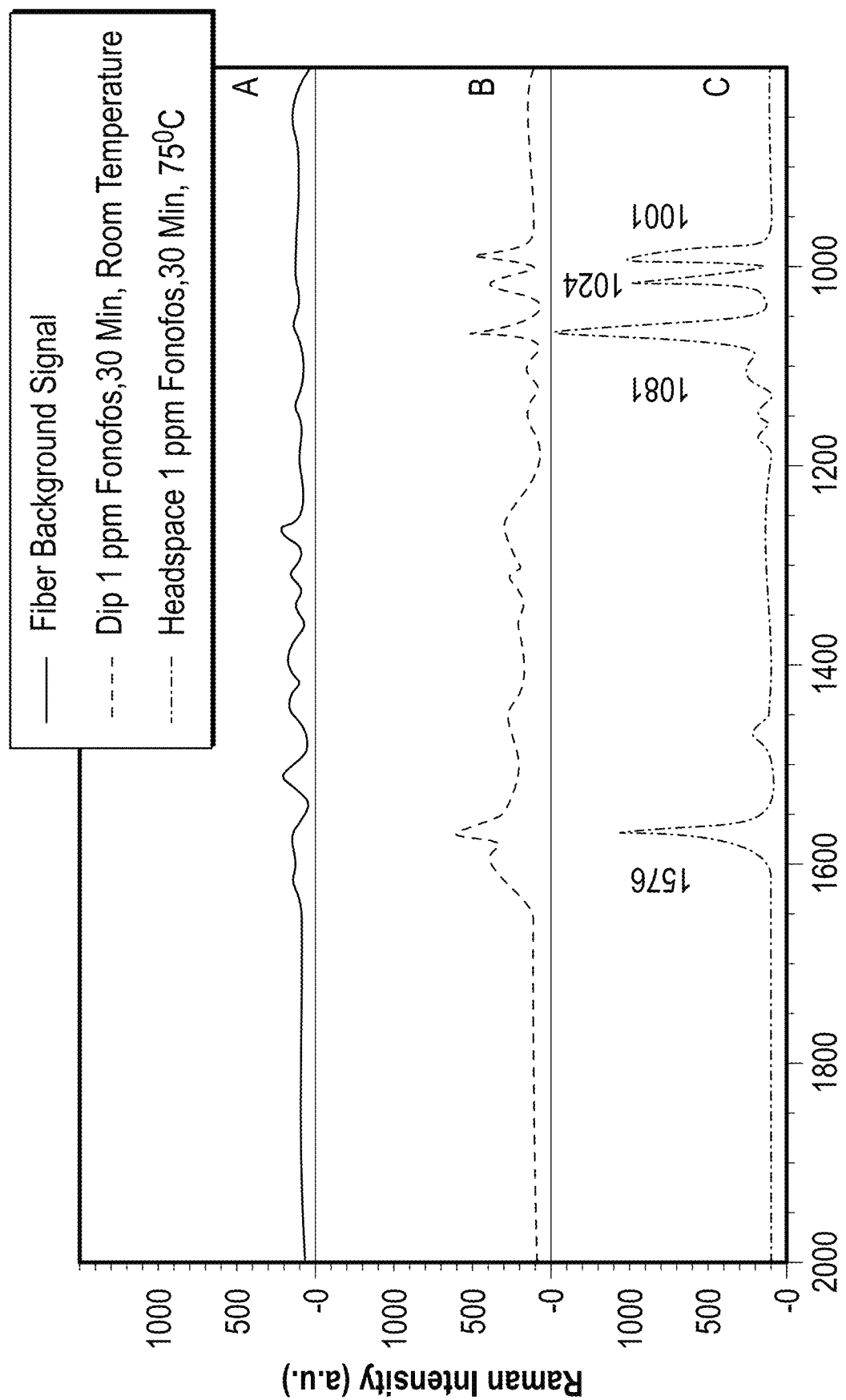
FIG. 5 shows spectra generated from the surface enhanced Raman scattering substrate assembly, in accordance with various embodiments.

After the fiber was fabricated, its SERS-active capability and extraction efficiency were tested in 1 ppm fonofos water solution with dip and headspace methods. In headspace-SPME approach, 20% NaCl solution was added to the sample as the addition of salt usually increases the ionic strengths and decreases the solubility of organic analytes in the aqueous phase. From FIG. 5, the fiber has minimal background noise between 800 to 2000 $cm^{-1}$ Raman shift, providing no interference to pesticide signals. In dip and headspace tests, the four most obvious peaks of fonofos on 1001, 1024, 1081 and 1576 $cm^{-1}$ Raman shift were observed and characterized in FIG. 5. The peak at 1576 $cm^{-1}$ is attributed to v(C=C) phenyl stretch which is used for quantitative analysis later. The peaks at 1081, 1024 and 1001 $cm^{-1}$ are respectively attributed to v(S—C phenyl)+δ(C—H)phenyl, δ(C—H)phenyl+v(S—C phenyl), and δ(CCC) phenyl (20). Moreover, headspace method presents higher intensity of signals and minimal interference compared to dip method, indicating the advantage and feasibility of headspace approach for fonofos detection.

Figure 6A:
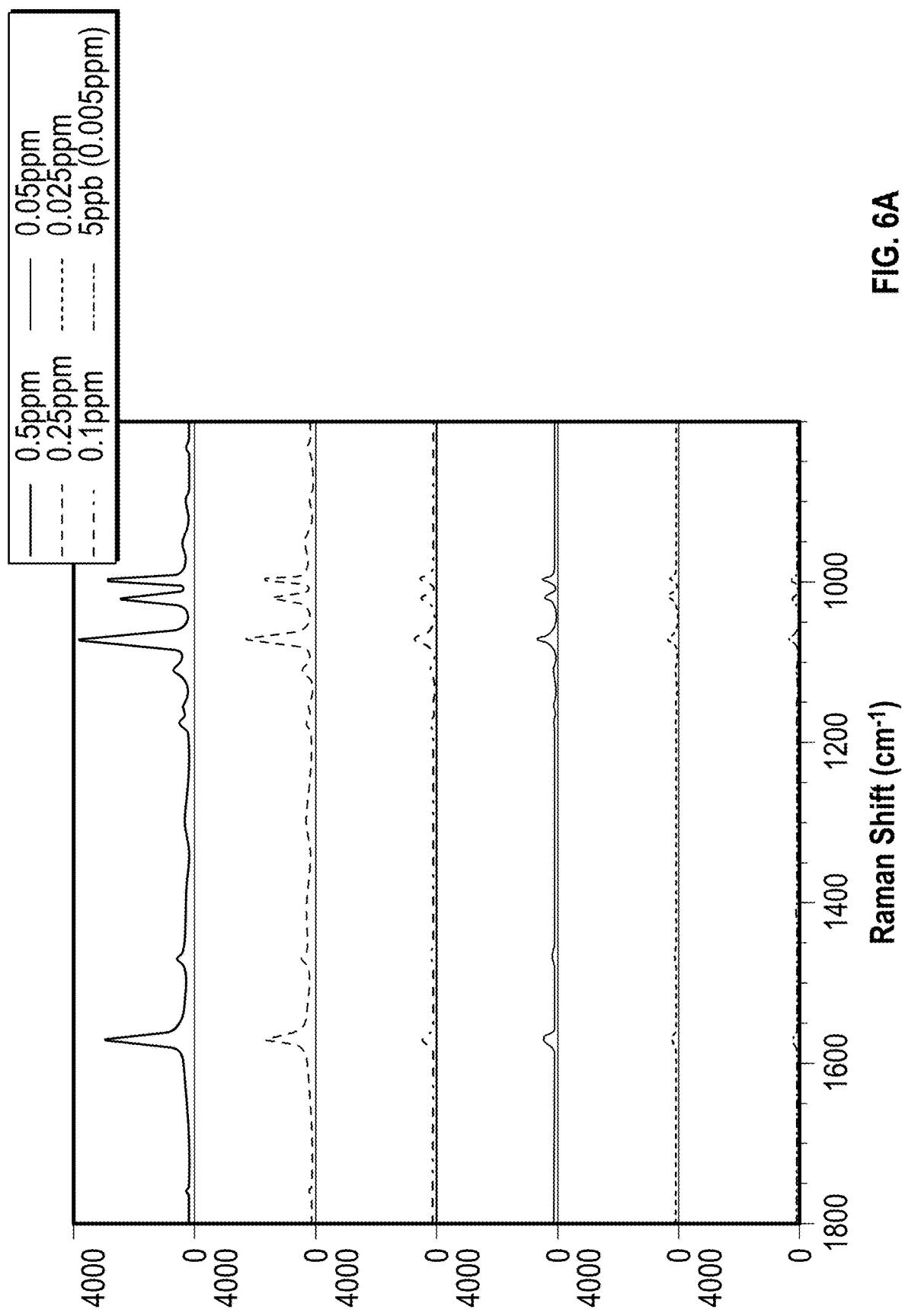
FIGS. 6A-6B are a spectrum and concentration chart generated from the surface enhanced Raman scattering substrate assembly, in accordance with various embodiments.
Figure 6B:
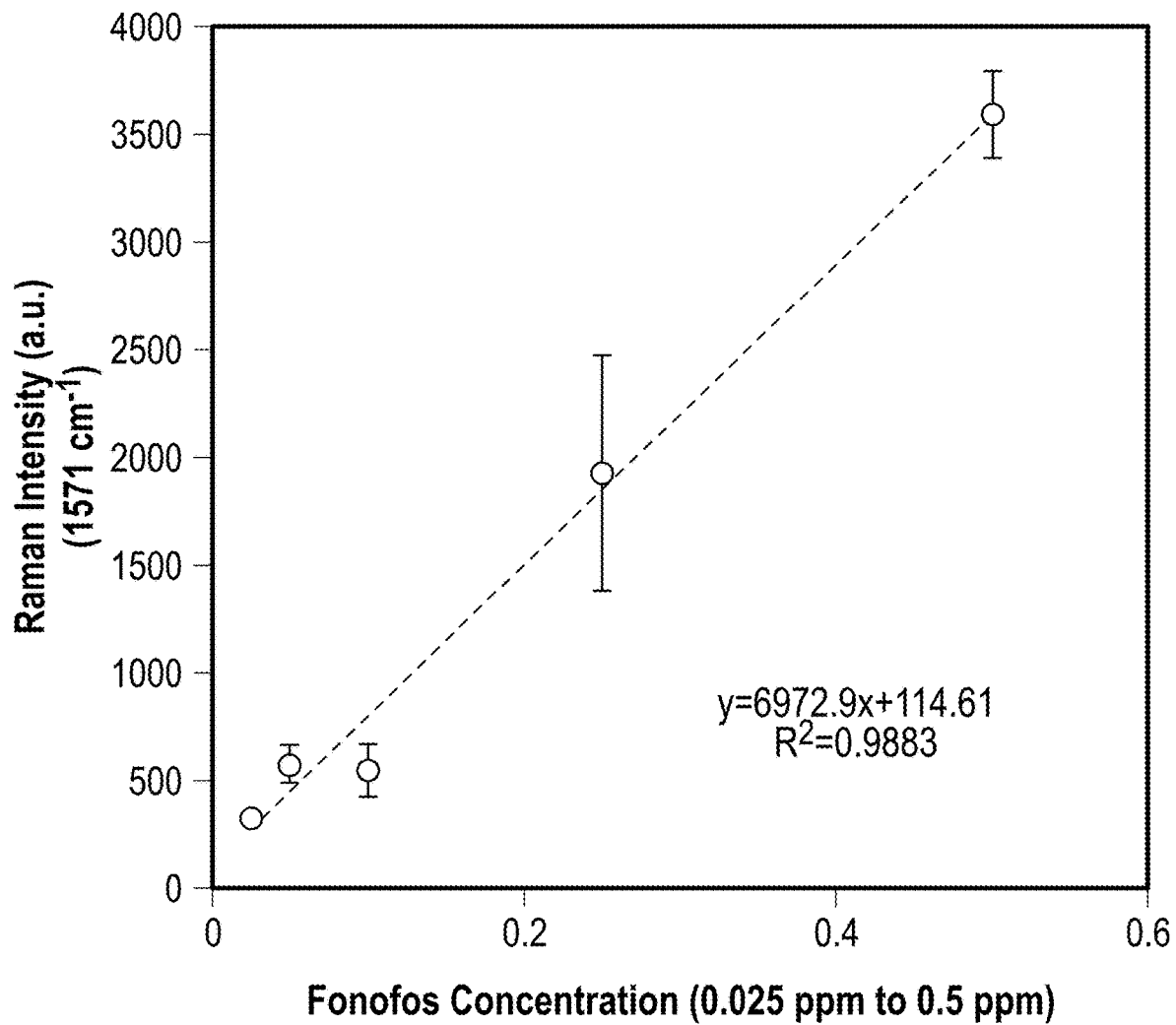

To investigate the sensitivity and quantitative reliability of the method, the headspace-SPME-SERS were applied to detect fonofos of various concentrations (0.005 ppm to 0.5 ppm) in water as shown FIG. 6A. The lowest detectable concentration at 5 ppb (0.005 ppm) was reached. Current SERS studies in detecting fonofos report higher detectable concentration at 10 ppm, and their limit of detection ranges from 0.1 ppm to 1 ppm. In comparison, the disclosed method offers a huge improvement on sensitivity due to the use of the headspace method for capturing volatile fonofos. Peak intensity at 1576 $cm^{-1}$ was selected for quantitative analysis and the linear range was obtained from 0.025 ppm to 0.5 ppm in FIG. 6B, Fonofos concentration and Raman intensity present a nice linear relation with coefficient of determination ($R^2$) as 0.9883. The Limit of Detection (LOD) value was calculated to be 0.0052 ppm according to the equation of 3.3 σ/S, where σ is the standard deviation of the blank, and S is the slope of the calibration curve. The LOD value is confirmed by the detection of 0.005 ppm (5 ppb) fonofos in FIG. 6A. The theoretical Limit of Quantification (LOQ) value can be extended to 0.015 ppm according to the equation of 10 σ/S. Yet, the error bars revealed that the method had large variations that needs to be further reduced. The variation may conic from varied sizes and aggregations of the gold-nanoparticles on the fiber which may be improved by using a stainless wire fiber with a higher quality and purity and further optimizing the coating reaction conditions.

Figure 7A:
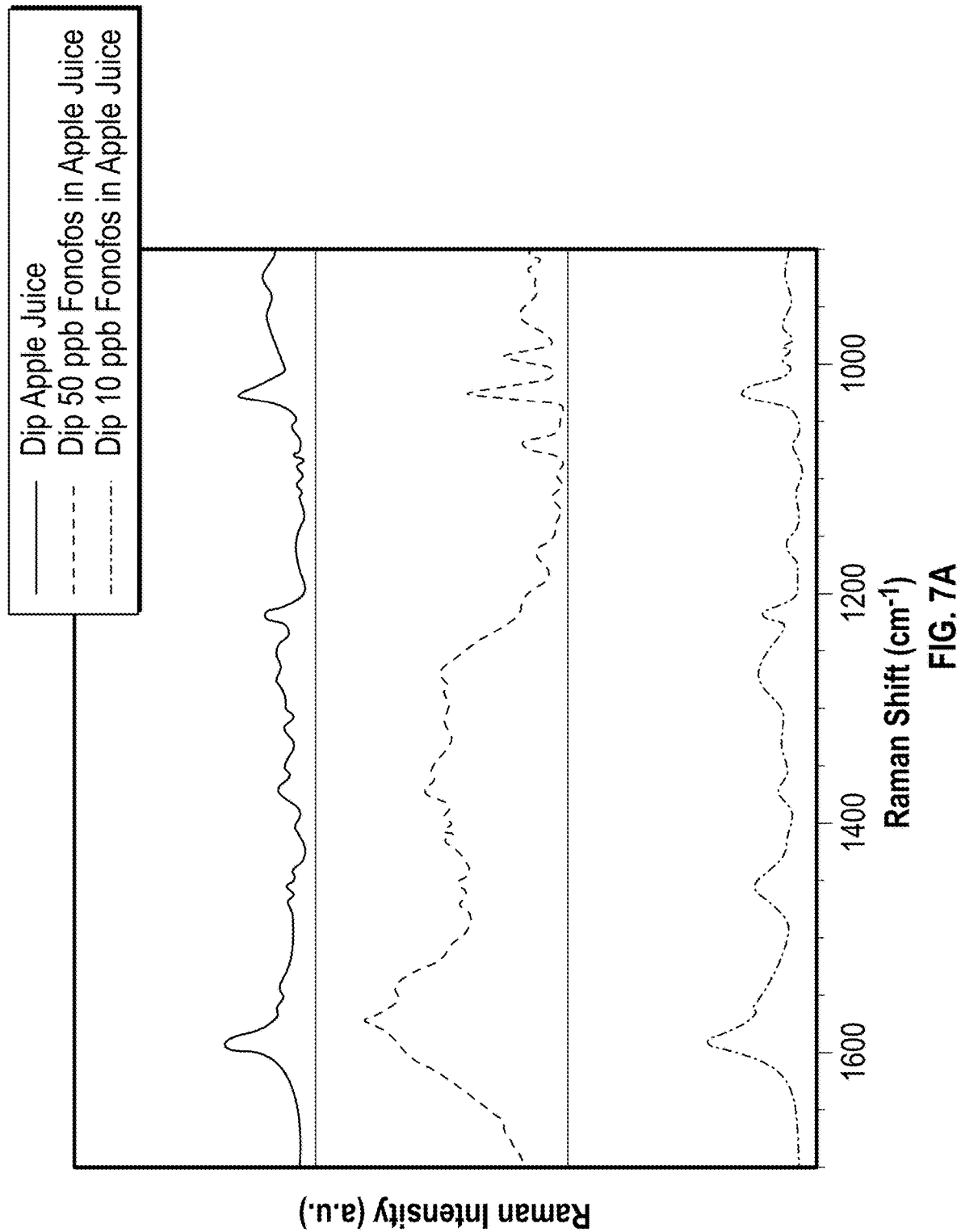
FIGS. 7A-7B are spectra generated from the surface enhanced Raman scattering substrate assembly, in accordance with various embodiments.
Figure 7B:
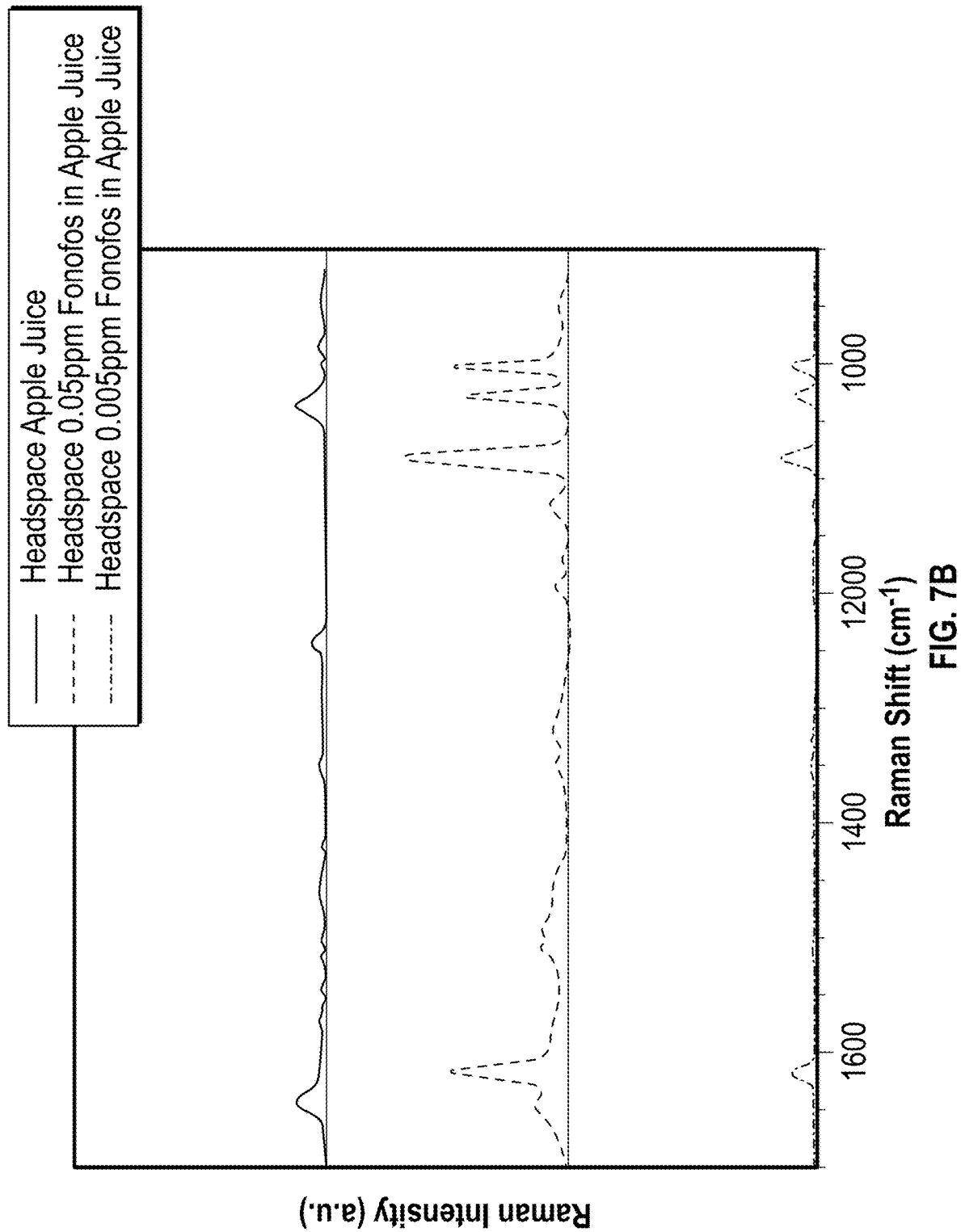

To further illustrate the advantage of headspace method in detecting a volatile pesticide in a real matrix, the headspace method was applied and compared with the dip method to detect fonofos in apple juice. From FIG. 7A, the dip-SPME-SERS method detected 50 ppb fonofos spiked in apple juice and cannot detect lower concentration at 10 ppb because it was affected by the inferencing compounds from apple juice. On the other hand, headspace-SPME-SERS detected 5 ppb fonofos spiked in apple juice (FIG. 7B). This data demonstrates the headspace method is more sensitive and effective than the dip method when detecting fonofos in complex matrices. It is because in the headspace, only volatile compounds occupy the space and have the chance to bind to the fiber. While in the dip detection, other components from the sample matrix may bind to the fiber and cause interference. The lowest detectable concentration at 5 ppb in a food sample is comparable to the nano-liquid chromatography and the common GC method in complex samples detection, which are 5.3 ppb and 30 ppb, respectively.

Example 2

SERS techniques were applied to monitor plant metabolites and physiological changes to provide insight into biochemical plant responses to biotic stress. The study was used to monitor SERS signals of salicylic acid (SA), nicotinamide adenine dinucleotide phosphate oxidase (NADPH oxidase), and camalexin. Each molecule is SERS sensitive and each SERS fingerprint is different based on their chemical structures. This allows for sensitive and selective monitoring of response signals in plant matrixes without overlap in spectral analyses. The presence of NADPH oxidase is also associated with reactive oxide species (ROS) and SA and emerges rapidly within a host. NADPH oxidase and SERS analyses allow for detection of plant responses to biotic stress within minutes. The presence of camalexin specifically indicates a plant response to biotic stress and this relationship can be assessed using SERS.

Tomato plant (*Solarium lycopersicum*) was fostered as a model. *Fusarium prolileratum*, a common tomato plant pathogen, was administered onto the surface of the plant tissues. The plant response was monitored in real-time in-situ locally and systemically with a field-based portable Raman instrument. SERS detection was performed by adding penetrable Gold nanoparticles (AuNPs) onto the surface of leaves or flowers. On fruits, a smart 'SERS needle' device was utilized which is composed of a real clinical needle and an inserted AuNP's coated fiber. SERS detection can be carried out by removing the fiber from the plant tissue for fiber-based collections of SERS spectra. The SERS needle device also allows for the injection of biotic stress factors directly into the fruit using a syringe wherein it is possible to monitor biomolecular stress responses in real-time locally or systemically.

Example 3

Figure 8:
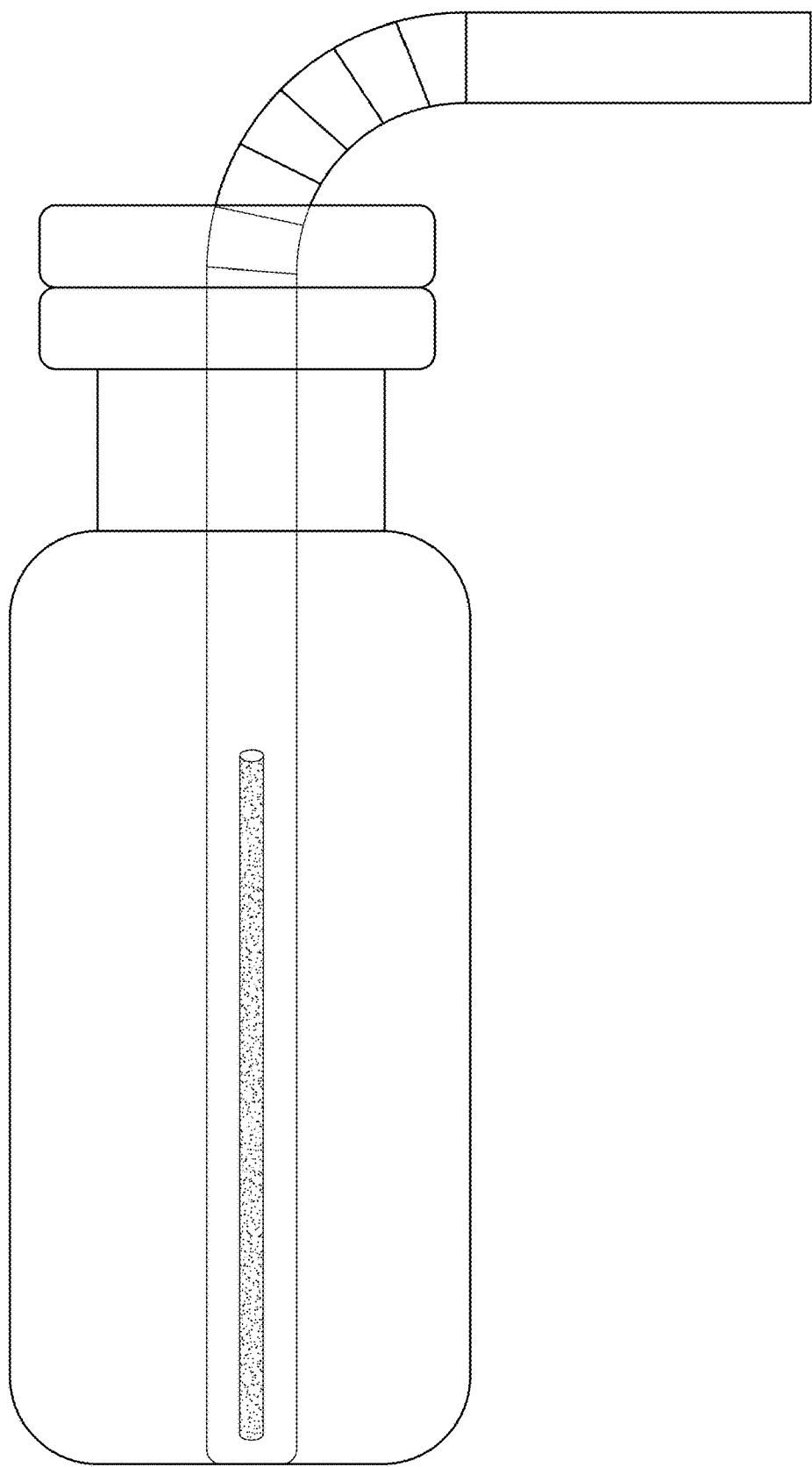
FIG. 8 is a surface enhanced Raman scattering substrate assembly, in accordance with various embodiments.
Figure 9:
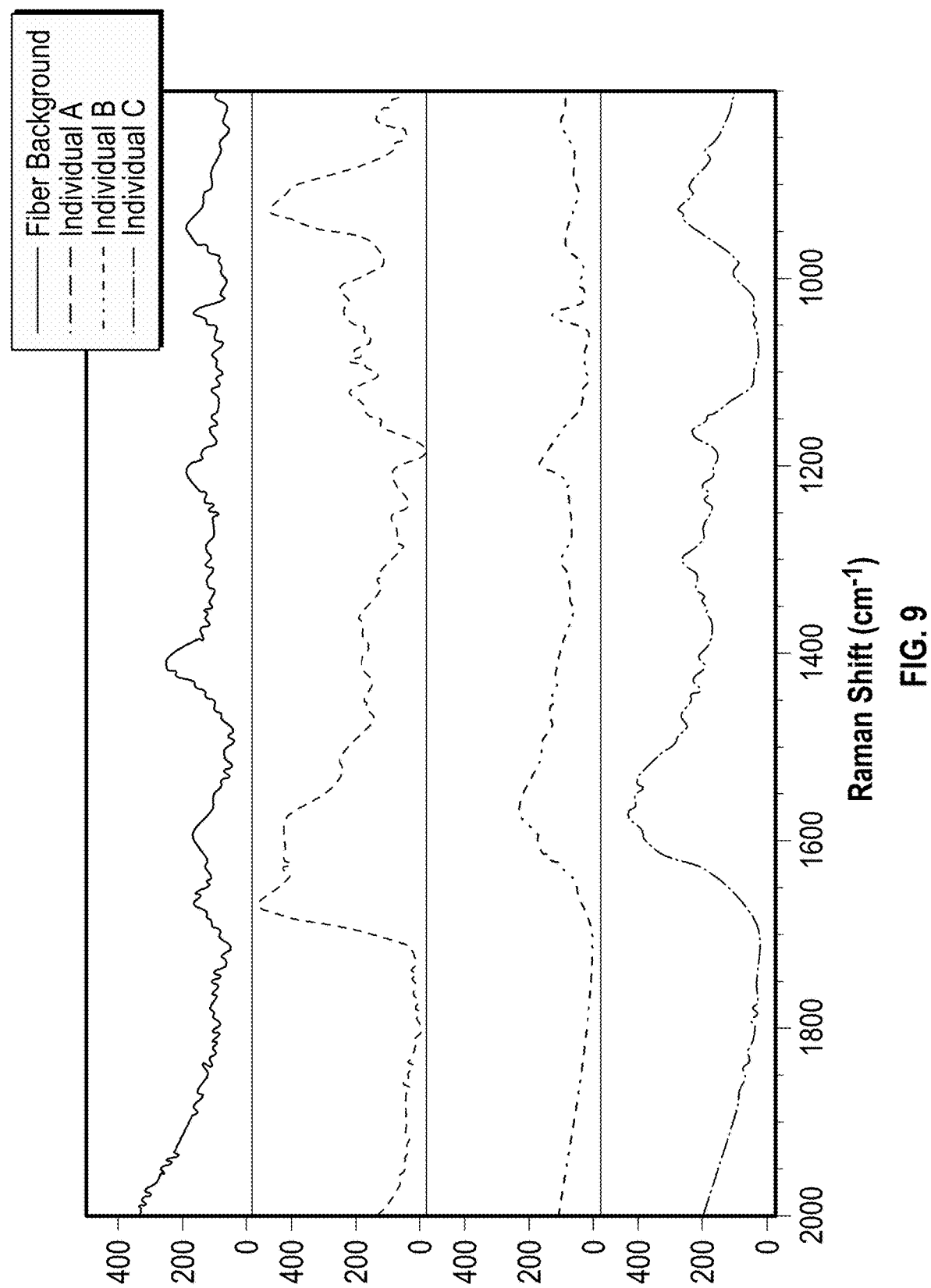
FIG. 9 are spectra generated from the surface enhanced Raman scattering substrate assembly, in accordance with various embodiments.

To analyze a person's breath a straw was inserted into a vial, with the gold-nanoparticles coated fiber put inside the straw. This assembly is shown in FIG. 8. Three individuals were asked to blow in the straw for 1 minute. Then the straw was folded to seal the breathing gas, and the fiber could be fully exposed to the gas. After 5 minutes of exposure and extraction, the fiber was measured with Raman scattering with 5 mW laser power. Resulting spectra are shown in FIG. 9.

Example 4

Figure 10:
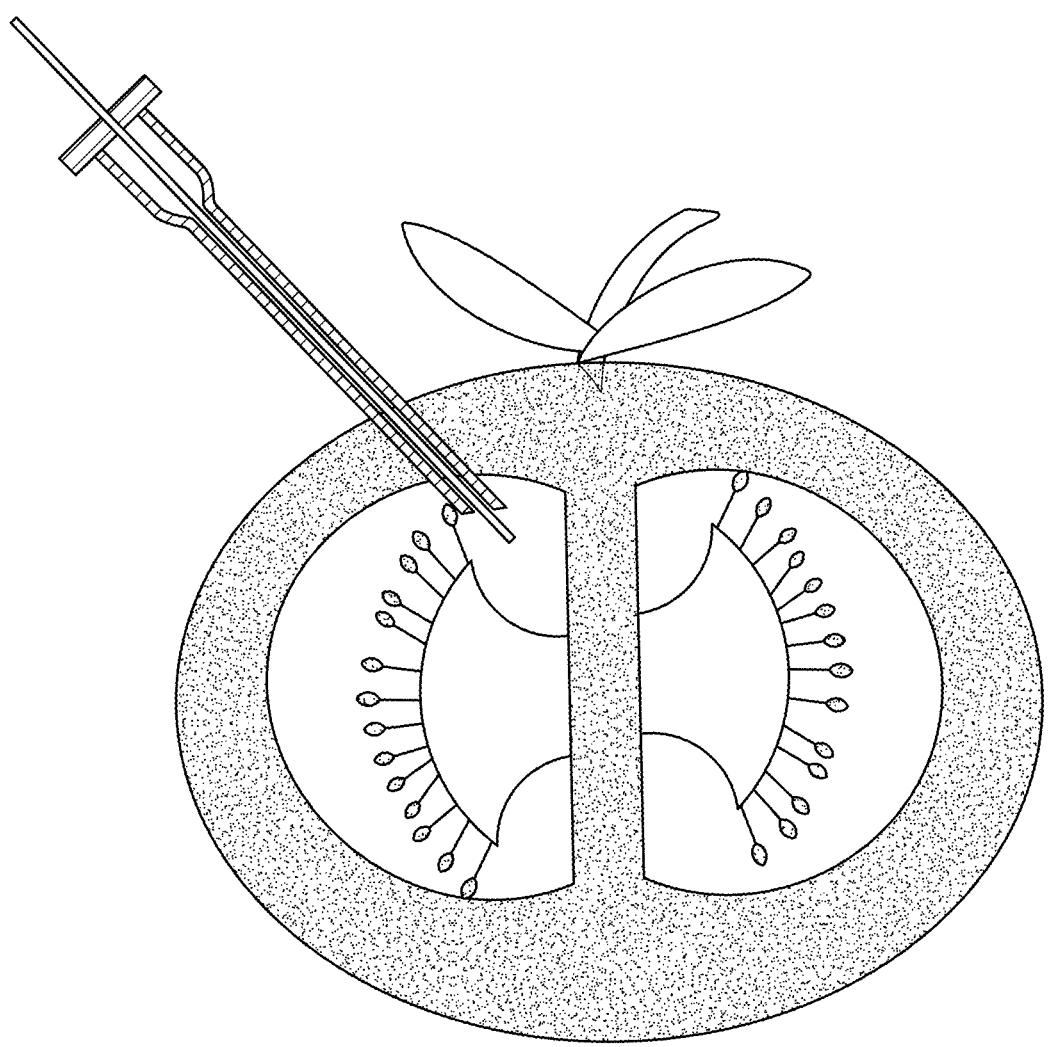
FIG. 10 is a schematic depiction of the surface enhanced Raman scattering substrate assembly located partially within a tomato, in accordance with various embodiments.

To detect the presence of an analyte such as a pesticide in food a surface enhanced Raman scattering substrate assembly was placed partially within a tomato. This is schematically shown in FIG. 10. As shown in FIG. 10, the needle is positioned within a solid phase, liquid phase, and gaseous (e.g., headspace) phase of the tomato.

Figure 11:
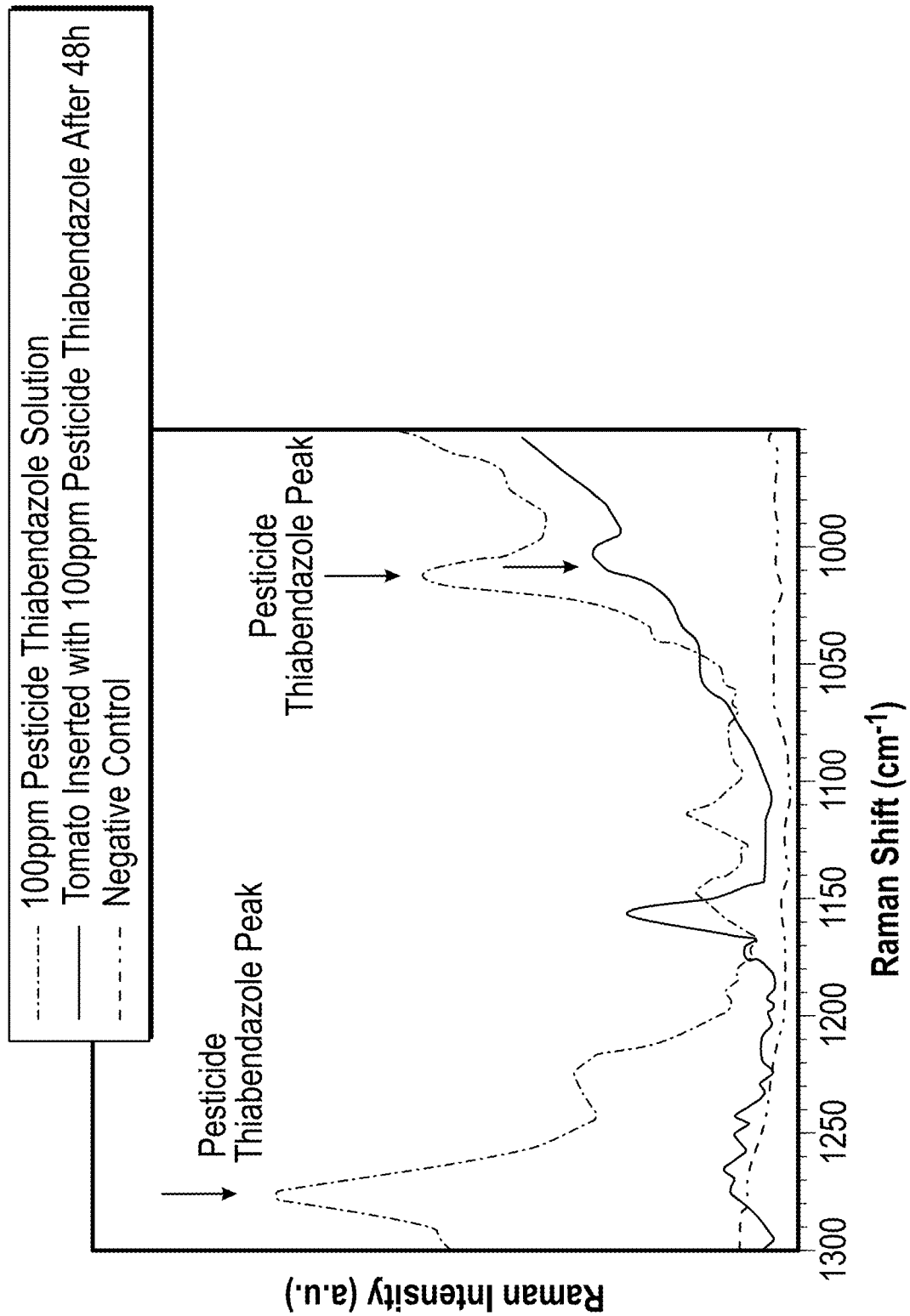
FIG. 11 is a spectrum generated from the surface enhanced Raman scattering substrate assembly deployed in the tomato of FIG. 10, in accordance with various embodiments.

100 ppm of the pesticide thiabendazole was injected on one side of the tomato. The pesticide was left to translocate through the tomato for a time period of 48 hours. After 48 hours, the surface enhanced Raman scattering substrate was used to detect the presence of the pesticide in the tomato. Detection was performed across the solid, liquid, and gaseous phases although detection can be optionally limited to any one phase of sub-combination of phases. FIG. 11 is a spectrum showing the presence of thiabendazole in the tomato.

Example 5

In Example 5, an in-situ filter was synthesized in a needle via in-situ polymerization using a high internal phase emulsion (HIPE) technique. First, dicyclopentadiene (DCPD) was pre-mixed with (poly(ethylene glycol)-block-polypropylene glycol)-block-poly(ethylene glycol (Pluronic1L-121) to create a mixture. Then, deionized water (DI) (16 mL) was added dropwise to the mixture under constant stirring to form high-internal phase emulsion. A solution of (H2IMes)(PCy3)Cl2Ru(3-phenyl-indenylid-1-ene) (M2) in toluene was added to the solution as a catalyst.

The mixed emulsion was withdrawn into a needle shell and cured in-situ at 80° C. The cured DCPD polymer formed a porous polymer network was used as an in-situ filter. Prior to application, the cured HIPE filter was washed in acetone to remove any un-cured monomers. The in-situ filter made in Example 5 can be seen in FIG. 12. Alternative monomeric compounds could be used for in-situ filter synthesis, such as divinylbenzene (DVB), 2-ethylhexyl acrylate (EHA) and methacrylate (EHMA), butyl acrylate (BA) and isobornyl acrylate (IBA), methyl methacrylate (MMA), and vinyllbenzyl chloride (VBC). An etched fiber could then be inserted into the needle with the DCPD filter for use in SERS analysis.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Embodiment 1 provides a surface enhanced Raman scattering substrate assembly for detecting an analyte, the assembly comprising:
an etched fiber base;
a metallic nanoparticle coating disposed over at least a portion of an external surface of the etched fiber base.

Embodiment 2 provides the assembly of Embodiment 1, wherein the etched fiber base comprises stainless steel, copper, lead, chromium, tin, magnesium, aluminum, zinc, manganese, calcium, alloys thereof, and mixtures thereof.

Embodiment 3 provides the assembly of any one of Embodiments 1 or 2, wherein the etched fiber base is acid-etched.

Embodiment 4 provides the assembly of any one of Embodiments 1-3, wherein the metallic nanoparticle coating is disposed over about 50% to about 100% of the total surface area of the etched fiber base.

Embodiment 5 provides the assembly of any one of Embodiments 1-4, wherein the metallic nanoparticle coating is dispersed over about 70% to about 100% of the total surface area of the etched fiber base.

Embodiment 6 provides the assembly of any one of Embodiments 1-5, wherein the metallic nanoparticle coating is dispersed over about 90% to about 98% of the total surface area of the etched fiber base.

Embodiment 7 provides the assembly of any one of Embodiments 1-6, wherein a surface area of the etched fiber base is greater than a corresponding fiber base that is free of etching.

Embodiment 8 provides the assembly of any one of Embodiments 1-7, wherein the etched fiber base has a length ranging from about 3 cm to about 6 cm.

Embodiment 9 provides the assembly of any one of Embodiments 1-8, wherein the etched fiber base has a length ranging from about 4 cm to about 5 cm.

Embodiment 10 provides the assembly of any one of Embodiments 1-9, wherein the etched fiber base has a width ranging from about 100 µm to about 400 µm.

Embodiment 11 provides the assembly of any one of Embodiments 1-9, wherein the etched fiber base has a width ranging from about 0.5 cm to about 5 cm.

Embodiment 12 provides the assembly of any one of Embodiments 1-11, wherein the etched fiber base is substantially cylindrically shaped.

Embodiment 13 provides the assembly of any one of Embodiments 1-12, wherein the metallic nanoparticle coating comprises a plurality of metallic nanoparticles.

Embodiment 14 provides the assembly of any one of Embodiments 1-13, wherein each of the plurality of metallic nanoparticles, independently comprise $Ag_2O$, elemental silver, elemental gold, elemental copper, elemental platinum, mixtures thereof, alloys thereof, or combinations thereof.

Embodiment 15 provides the assembly of any one of Embodiments 1-14, wherein each of the plurality of metallic nanoparticles comprises elemental gold.

Embodiment 16 provides the assembly of any one of Embodiments 1-15, wherein at least one of the plurality of metallic nanoparticles is a nanosphere, a nanochain, a nanoreef, a nanobox, or a nanostar.

Embodiment 17 provides the assembly of any one of Embodiments 1-16, wherein a largest dimension of at least one of the plurality of metallic nanoparticles has a largest dimension in a range of from about 25 nm to about 500 nm.

Embodiment 18 provides the assembly of any one of Embodiments 1-17, wherein a largest dimension of at least one of the plurality of metallic nanoparticles has a largest dimension in a range of from about 50 nm to about 100 nm.

Embodiment 19 provides the assembly of any one of Embodiments 1-18, further comprising a metallic microparticle coating dispersed over at least a portion of the surface of the etched fiber base.

Embodiment 20 provides the assembly of any one of Embodiments 1-19, further comprising a needle circumscribing at least a portion of the fiber base.

Embodiment 21 provides the assembly of Embodiment 20, wherein the needle comprises a metal.

Embodiment 22 provides the assembly of any one of Embodiments 1-21, wherein the assembly is further configured to detect the analyte in at least one of a gaseous phase, a liquid phase and a solid phase.

Embodiment 23 provides the assembly of any one of Embodiments 1-22, wherein the analyte is chosen from a pesticide, a metabolite, a pathogen, a bacteria, a fungi, a virus, an enzyme, a reactive oxygen species, and a mixture thereof.

Embodiment 24 provides the assembly of Embodiment 23, wherein the pesticide is chosen from O-Ethyl S-phenyl ethylphosphonodithioate, thiabendazole, acetamiprid, iron tris(dimethidithiocarbamate), phosmet, phorate, isocarbophos, and mixtures thereof.

Embodiment 25 provides the assembly of Embodiment 23, wherein the metabolite is chosen from salicylic acid, phytoalexin, sulfonic acid, diphenyl sulfide, allyl methyl sulfide, and a mixture thereof.

Embodiment 26 provides the assembly of Embodiment 23, wherein the enzyme is chosen from flavin adenine dinucleotide, nicotinamide adenine dinucleotide phosphate oxidase, and mixtures thereof.

Embodiment 27 provides the assembly of Embodiment 23, wherein the bacteria is chosen from a gram-positive bacteria, a gram-negative bacteria, and mixtures thereof.

Embodiment 28 provides the assembly of Embodiment 27, wherein the bacteria is chosen from *Clostridium botulinum, Listeria monocytogenes, Acetic acid bacteria, Acidaminococcus, Acinetobacter baumannii, Agrobacterium tumefitciens, Akkermansia Anaerobiospirillum, Anaerolinea thermolimosa, Anaerolinea thermophila, Arcobacter, Arcobacter skirrowii, Armatimonas rosea, Azotobacter salinestris, Bacteroides, Bacteroides fragilis, Bacteroides ureolyticus, Bacieroidetes, Bartonella japonica, Bartonella koehlerae, Bartonella Bdellovibrio, Brachyspira, Bradyrhizobium japonicum, Caldilinea aerophile, Cardiobacterium hominis, Chaperone-Usher fimbriae, Christensertella, Chthonomonas calidirosea, Coxiella burnetiid, Cyanobacteria, Cytophaga, Dehalogenimonas lykanthroporepellens, Desulfitrobacterium atlanticum, Devosia pactfica, Devosia psychrophila, Devosia soli, Devosia suhaequoris, Devosia submarina, Devosia yakushimensis, Dialister, Dictyoglomus thermophilum, Enterobacter, Enterobacter cloacae, Enterobacter cowanii Enterobacteriaceae, Emerobacteriales, Escherichia, Escherichia coli, Escherichia fergusonii, Escherichia hermannii, Fimbriimonas ginsengisoli, Flavobacterium, Flavobacterium akiainvivens, Francisella novicida, Fusobacterium necrophorum, Fusobacterium nucleatum, Fusobacterium polymorphum, Haemophilia felis, Haemophilus haemolyticus, Haemophilus influenzae, Haemophilus pittmaniae, Helicobacter, Kingella kingae, Klebsiella pneumoniae, Kluyvera ascorbate, Kluyvera cryocrescens, Legionella, Legionella clemsonensis, Legionella pneumophila, Leptonema illini, Leptotrichia buccalis, Levilinea saccharolyuica, Luteimonas aquatic, Luteimonas composti, Luteimonas lutimaris, Luteimonas marina, Luteimonas mephitis, Luteimonas vadose, Megamonas, Megasphaera, Meiothermus, Meiothermus timidus, Methylobacterium fujisawaense, Morax-Axenfeld diplobacilli, Moraxella, Moraxella bovis, Moraxella osloensis, Morganella morganii, Mycoplasma spumans, Neisseria cinereal, Neisseria gonorrhoeae, Neisseria meningitidis, Neisseria polysaccharea Neisseria sicca, Nitrosomonas eutropha, Nitrosomonas halophila, Nonpathogenic organisms, OMPdb, Pectinatus, Pedohacter heparinus, Pelosinus, Propionispora, Proteobacteria, Proteus mirabilis, Proteus penneri, Pseudomonas, Pseudomonas aeruginosa, Pseudomonas luteola, Pseudoxanthomonas broegbernensis, Pseudoxanthomonas japonensis, Rickettsia rickettsia, Salinibacter ruber, Salmonella, Salmonella bongori, Salmonella enterica, Samsonia, Selenomonadales, Serratia marcescens, Shigella, Shimwellia, Solobacierium moorei, Sporangium cellulosum, Sphaerotilus natans, Sphingomonas gei, Spirochaeta, Spirochaetaceae, Sporomusa, Stenotrophomonas, Stenotrophomonas nitritireducens, Thermotoga neapolitana, Thorselliaceae, Trimeric autotramporter adhesion, Vampirococcus, Verminephrobacter, Vibrio adaptatus, Vibrio azasnii, Vibrio campbellii, Vibrio cholerae, Victivallis vadensis, Vitreoscilla, Wolhachia, Yersiniaceae, Zymophilus*, strains thereof, and mixtures thereof.

Embodiment 29 provides the assembly of any one of Embodiments 1-28, wherein the analyte is located in a medium.

Embodiment 30 provides the assembly of Embodiment 29, wherein the medium comprises a food, a beverage, a plant, an animal, or a mixture thereof.

Embodiment 31 provides the assembly of Embodiment 30, wherein the food is chosen from a vegetable, a fruit, a meat, a dairy product, a grain, and mixtures thereof.

Embodiment 32 provides the assembly of Embodiment 30, wherein the beverage is chosen from milk, beer, wine, water, juice, coffee, tea, and mixtures thereof.

Embodiment 33 provides the assembly of any one of Embodiments 1-32, further comprising:
a source of electromagnetic radiation in optical communication with the metallic nanoparticle coating; and
a detector for detecting a signal from the metallic nanoparticle coating.

Embodiment 34 provides a method for detecting an analyte, the method comprising:
contacting the etched fiber base of any one of Embodiments 1-33 with the medium of any one of Embodiments 29-33;
contacting the medium with an electromagnetic emission;
detecting the analyte; and
generating a spectrum.

Embodiment 35 provides the method of Embodiment 34, further comprising identifying an analyte in the medium from the spectrum.

Embodiment 36 provides the method of Embodiment 35, further comprising quantifying an amount of analyte present in the medium from the spectrum.

Embodiment 37 provides the method of any one of Embodiments 34-36, wherein the etched fiber base is located in at least one of a gaseous phase, a liquid phase, or a solid phase.

Embodiment 38 provides the method of any one of Embodiments 34-37, wherein the etched fiber base and the medium are located in a sealed environment.

Embodiment 39 provides the method of any one of Embodiments 34-38, wherein the electromagnetic emission is a laser emission.

Embodiment 40 provides the method of any one of Embodiments 34-39, wherein the analyte is an indicator of a response to biotic stress.

Embodiment 41 provides the method of any one of Embodiments 34-40, further comprising heating the analyte to a temperature sufficient to put the analyte into a gaseous phase.

Embodiment 42 provides a method of making the assembly of any one of Embodiments 1-41, the method comprising:
etching a fiber to form the etched fiber base; and
coating the metallic nanoparticles on the surface of the etched fiber base.

Embodiment 43 provides the method of Embodiment 42, wherein the fiber is etched by exposing the fiber to an etchant.

Embodiment 44 provides the method of Embodiment 43, wherein the etchant is an acid.

Embodiment 45 provides the method of any one of Embodiments 43 or 44, wherein the acid is hydrochloric acid.

Embodiment 46 provides the method of any one of Embodiments 42-45, wherein coating the metallic nanoparticles on the surface of the etched fiber base comprises at least partially immersing the etched fiber base in a solution comprising the metal of the metallic nanoparticle and reducing the metal in the solution.

Embodiment 47 provides the method of Embodiment 46, wherein the solution comprises $HAuCl_4$.

Embodiment 48 provides the assembly of Embodiment 1, further comprising a needle circumscribing at least a portion of the fiber base, and an in-situ filter in the needle.

Embodiment 49 provides the assembly of Embodiment 1, wherein the in-situ filter comprises of cellulose, nitrocellulose, polytetrafluoroethylene (PTFE), nylon, polycarbonate, acrylic based polymers, methacrylic based polymers, and combinations thereof.

Embodiment 50 provides the assembly of Embodiment 1, wherein the in-situ filter comprises a plurality of pores each having a size of about 5 μm to about 35 μm.

Embodiment 51 provides the assembly of Embodiment 50, wherein the in-situ filter comprises a plurality of pores each having a size of about 10 μm to about 25 μm.

Embodiment 52 provides the assembly of Embodiment 1, wherein the in-situ filter is configured to filter impurities out of the medium.

Embodiment 53 provides the assembly of Embodiment 1, wherein the in-situ filter is configured to prevent impurities from reaching the fiber base.

Embodiment 54 provides the assembly of Embodiment 1, wherein the in-situ filter is located in an end of the needle.

Embodiment 55 provides the assembly of Embodiment 1, wherein the in-situ filter is located along the walls of the needle.

What is claimed is:

1. A surface enhanced Raman scattering substrate assembly for detecting an analyte, the assembly comprising:
    an etched fiber base;
    a metallic nanoparticle coating disposed over at least a portion of an external surface of the etched fiber base, the metallic nanoparticle coating comprising metallic nanoparticles that have a largest dimension of 25 nm to about 500 nm; and
    a needle circumscribing at least a portion of the etched fiber base.

2. The assembly of claim 1, wherein the etched fiber base comprises stainless steel, copper, lead, chromium, tin, magnesium, aluminum, zinc, manganese, calcium, alloys thereof, or combinations thereof.

3. The assembly of claim 1, wherein the metallic nanoparticle coating is disposed over about 50% to about 100% of the total surface area of the etched fiber base.

4. The assembly of claim 1, wherein a surface area of the etched fiber base is greater than a corresponding fiber base that is free of etching.

5. The assembly of claim 1, wherein the etched fiber base has a length ranging from about 3 cm to about 6 cm.

6. The assembly of claim 1, wherein the etched fiber base has a width ranging from about 100 μm to about 400 μm.

7. The assembly of claim 1, wherein the etched fiber base is substantially cylindrically shaped.

8. The assembly of claim 1, wherein the metallic nanoparticles each independently comprise $Ag_2O$, elemental silver, elemental gold, elemental copper, elemental platinum, mixtures thereof, alloys thereof, or combinations thereof.

9. The assembly of any one of claim 1, wherein the metallic nanoparticles have a largest dimension of about 50 nm to about 100 nm.

10. The assembly of claim 1, further comprising a metallic microparticle coating dispersed over at least a portion of the surface of the etched fiber base.

11. The assembly of any one of claim 1, wherein the assembly is configured to detect the analyte in a gaseous phase, a liquid phase, a solid phase, or a combination thereof.

12. The assembly of claim 1, further comprising:
    an in-situ filter in the needle.

13. The assembly of claim 12, wherein the in-situ filter comprises of cellulose, nitrocellulose, polytetrafluoroethylene (PTFE), nylon, polycarbonate, acrylic based polymers, methacrylic based polymers, and combinations thereof.

14. The assembly of claim 12, wherein the in-situ filter is located in a tip of the needle.

15. The assembly of claim 12, wherein the in-situ filter is located along one or more walls of the needle.

16. A method for detecting an analyte, the method comprising:
    contacting an etched fiber base with a medium to collect the analyte from the medium on the etched fiber base, wherein a metallic nanoparticle coating is disposed over at least a portion of an external surface of the etched fiber base, the metallic nanoparticle coating comprising metallic nanoparticles that have a largest dimension of 25 nm to about 500 nm, wherein a needle circumscribes at least a portion of the etched fiber base;
    contacting the etched fiber base comprising the analyte with an electromagnetic emission;
    detecting the analyte; and
    generating a spectrum.

17. The method of claim 16, further comprising identifying or quantifying an analyte in the medium from the spectrum.

18. The method of claim 16, wherein contacting the etched fiber base with the medium comprises puncturing a material with the needle to form an opening such that the etched fiber base collects the analyte from the medium.

19. A method of making an assembly comprising:
    etching a fiber to form an etched fiber base;
    coating metallic nanoparticles on an external surface of the etched fiber base, the metallic nanoparticle coating comprising metallic nanoparticles that have a largest dimension of 25 nm to about 500 nm; and
    circumscribing at least a portion of the etched fiber base with a needle.

* * * * *